(12) United States Patent
Naseri et al.

(10) Patent No.: US 10,993,645 B2
(45) Date of Patent: May 4, 2021

(54) SYSTEM AND METHOD FOR NON-INVASIVE ANALYSIS OF BODILY FLUIDS

(71) Applicant: Qurasense, Inc., Palo Alto, CA (US)

(72) Inventors: Sara Naseri, Stanford, CA (US); Søren Therkelsen, Woodside, CA (US)

(73) Assignee: QURASENSE INC., Palo Alto, CA (US)

( * ) Notice: Subject to any disclaimer, the term of this patent is extended or adjusted under 35 U.S.C. 154(b) by 592 days.

(21) Appl. No.: 15/505,537

(22) PCT Filed: Aug. 5, 2015

(86) PCT No.: PCT/US2015/043883
§ 371 (c)(1),
(2) Date: Feb. 21, 2017

(87) PCT Pub. No.: WO2016/028497
PCT Pub. Date: Feb. 25, 2016

(65) Prior Publication Data
US 2017/0265789 A1    Sep. 21, 2017

Related U.S. Application Data

(60) Provisional application No. 62/040,341, filed on Aug. 21, 2014.

(51) Int. Cl.
*A61B 5/00* (2006.01)
*A61B 5/1477* (2006.01)
(Continued)

(52) U.S. Cl.
CPC .......... *A61B 5/1477* (2013.01); *A61B 5/0022* (2013.01); *A61B 5/0024* (2013.01);
(Continued)

(58) Field of Classification Search
CPC .. A61K 35/74; A61K 35/741; A61K 2039/53; A61B 5/01; A61B 17/42;
(Continued)

(56) References Cited

U.S. PATENT DOCUMENTS 4,628,941 A * 12/1986 Kosasky ............ A61B 10/0291
600/572
4,800,896 A * 1/1989 Jalowayski ............ A61B 10/04
600/572
(Continued)

FOREIGN PATENT DOCUMENTS

DE    19837678 A1    3/2000
JP    2002-542843 A    12/2002
(Continued)

OTHER PUBLICATIONS

International Search Report and Written Opinion issued by the U.S. Patent and Trademark Office as International Searching Authority for International Application No. PCT/US15/43883 dated Nov. 12, 2015 (13 pages).
(Continued)

*Primary Examiner* — May A Abouelela
(74) *Attorney, Agent, or Firm* — Epstein Drangel LLP; Robert L. Epstein

(57) ABSTRACT

A vaginal fluid monitoring device includes an absorbent layer, wherein the absorbent layer is configured to be in proximity to flow of vaginal fluid; an electrochemical detection system configured to obtain data regarding at least one analyte in a vaginal fluid, said electrochemical detection system in fluid communication with the absorbent layer; and wherein the vaginal fluid monitoring device is configured to be coupled with a feminine hygiene product.

26 Claims, 21 Drawing Sheets

(51) Int. Cl.
| | | |
|---|---|---|
| A61B 10/00 | (2006.01) | |
| A61F 13/472 | (2006.01) | |
| A61F 13/42 | (2006.01) | |
| A61B 5/1468 | (2006.01) | |
| A61F 13/84 | (2006.01) | |
| A61B 5/145 | (2006.01) | |
| A61B 5/1495 | (2006.01) | |
| A61F 13/537 | (2006.01) | |

(52) U.S. Cl.
CPC .......... *A61B 5/1468* (2013.01); *A61B 5/1495* (2013.01); *A61B 5/14507* (2013.01); *A61B 5/14546* (2013.01); *A61B 5/4337* (2013.01); *A61B 10/0045* (2013.01); *A61F 13/42* (2013.01); *A61F 13/472* (2013.01); *A61F 13/537* (2013.01); *A61F 13/84* (2013.01); A61B 2010/0003 (2013.01); A61B 2010/0006 (2013.01); A61B 2010/0074 (2013.01); A61B 2560/0209 (2013.01); A61F 2013/424 (2013.01); A61F 2013/8473 (2013.01); A61F 2013/8479 (2013.01); A61F 2013/8482 (2013.01)

(58) Field of Classification Search
CPC .... A61B 2010/0074; A61B 2017/4216; A61B 10/0012; A61B 10/0045; A61B 1/303; A61B 2017/345; A61B 5/4337; A61B 10/0291; A61P 15/18; G01N 33/689; G01N 33/6893; G01N 33/48; G01N 33/54353; G01N 33/56983; G01N 33/57411; A61F 13/84; A61F 5/4553; A61F 13/472; A61F 2013/8473; A61F 13/15; A61F 13/202; A61F 13/2045; A61F 13/42; A61F 13/49
USPC .................... 600/300, 572, 584, 591; 435/12
See application file for complete search history.

(56) References Cited

U.S. PATENT DOCUMENTS

| | | | | |
|---|---|---|---|---|
| 4,953,563 | A * | 9/1990 | Kaiser | A61B 1/00142 600/591 |
| 5,063,930 | A * | 11/1991 | Nucci | A61B 10/0012 600/366 |
| 5,259,391 | A * | 11/1993 | Altshuler | A61B 10/0291 600/572 |
| 5,676,820 | A | 10/1997 | Wang et al. | |
| 5,735,801 | A * | 4/1998 | Caillouette | A61B 5/00 600/572 |
| 5,827,200 | A * | 10/1998 | Caillouette | A61B 10/02 600/584 |
| 5,916,176 | A * | 6/1999 | Caillouette | A61B 5/00 600/572 |
| 6,007,498 | A | 12/1999 | Buck et al. | |
| 6,013,036 | A * | 1/2000 | Caillouette | A61B 5/00 600/572 |
| 6,019,734 | A * | 2/2000 | Parkinson | G01N 33/56911 600/572 |
| 6,063,042 | A * | 5/2000 | Navot | A61F 13/42 600/584 |
| 6,126,597 | A * | 10/2000 | Smith | A61B 5/4294 600/309 |
| 6,149,590 | A * | 11/2000 | Smith | A61B 5/4294 600/367 |
| 6,352,513 | B1 * | 3/2002 | Anderson | A61B 10/0045 600/569 |
| 6,390,991 | B1 * | 5/2002 | Caillouette | A61B 5/14507 600/584 |
| 6,409,681 | B1 * | 6/2002 | Caillouette | A61B 5/14507 600/584 |
| 6,475,165 | B1 * | 11/2002 | Fournier | A61B 10/0291 600/562 |
| 7,458,941 | B2 * | 12/2008 | Caillouette | A61B 5/14507 600/572 |
| 7,666,148 | B1 * | 2/2010 | Caillouette | A61B 10/0045 600/570 |
| 7,771,366 | B2 * | 8/2010 | Kirsner | A61B 5/053 600/547 |
| 7,947,467 | B2 * | 5/2011 | Kritzman | A61B 5/14539 435/12 |
| 8,734,364 | B1 * | 5/2014 | Mantzaris | A61B 5/4362 600/572 |
| 8,911,988 | B2 | 12/2014 | Miller | |
| 9,110,053 | B2 * | 8/2015 | Cohen | B01L 3/5023 |
| 2001/0023321 | A1 * | 9/2001 | Gombrich | A61B 10/0291 600/562 |
| 2002/0007161 | A1 | 1/2002 | Bouchard et al. | |
| 2002/0032389 | A1 * | 3/2002 | Fournier | A61B 10/0291 600/572 |
| 2002/0058886 | A1 * | 5/2002 | Caillouette | A61B 5/00 600/572 |
| 2003/0017605 | A1 * | 1/2003 | Kritzman | A61B 5/14539 436/63 |
| 2003/0028123 | A1 * | 2/2003 | Pevoto | A61B 10/0045 600/562 |
| 2003/0166293 | A1 * | 9/2003 | Kritzman | A61B 5/14539 436/111 |
| 2004/0068162 | A1 * | 4/2004 | Kirsner | A61B 5/0002 600/300 |
| 2004/0106190 | A1 | 6/2004 | Yang et al. | |
| 2004/0220538 | A1 | 11/2004 | Panopoulos | |
| 2007/0003993 | A1 * | 1/2007 | Kritzman | A61B 5/14539 435/12 |
| 2007/0047568 | A1 | 3/2007 | Wang et al. | |
| 2007/0073192 | A1 * | 3/2007 | Caillouette | A61B 5/14507 600/584 |
| 2008/0009769 | A1 * | 1/2008 | Caillouette | A61B 5/14507 600/584 |
| 2008/0077097 | A1 | 3/2008 | Chambers et al. | |
| 2008/0269706 | A1 | 10/2008 | Long et al. | |
| 2009/0017474 | A1 * | 1/2009 | Maltzman | A61B 10/0045 435/7.23 |
| 2010/0222708 | A1 * | 9/2010 | Hitchcock | A61B 5/036 600/591 |
| 2011/0190595 | A1 * | 8/2011 | Bennett | A61B 1/00016 600/301 |
| 2011/0230743 | A1 | 9/2011 | Inciardi et al. | |
| 2012/0040655 | A1 | 2/2012 | Larkin | |
| 2012/0085645 | A1 | 4/2012 | Mousa et al. | |
| 2012/0130195 | A1 * | 5/2012 | Martin | A61B 5/14507 600/300 |
| 2012/0206265 | A1 | 8/2012 | Solazzo et al. | |
| 2013/0053657 | A1 * | 2/2013 | Ziarno | A61B 1/00016 600/304 |
| 2013/0165816 | A1 * | 6/2013 | Mor | A61F 13/505 600/582 |
| 2013/0254141 | A1 | 9/2013 | Barda et al. | |
| 2013/0289443 | A1 * | 10/2013 | Kim | A61B 10/0045 600/584 |
| 2013/0296739 | A1 | 11/2013 | Schultz | |
| 2013/0331666 | A1 | 12/2013 | Miller | |
| 2014/0066807 | A1 * | 3/2014 | Lundkvist | A61B 10/0096 600/572 |
| 2014/0121473 | A1 | 5/2014 | Banet et al. | |
| 2014/0121473 | A1 | 5/2014 | Faybishenko et al. | |
| 2014/0198203 | A1 | 7/2014 | Vardi et al. | |
| 2014/0200538 | A1 | 7/2014 | Euliano et al. | |
| 2014/0330167 | A1 * | 11/2014 | Speck | A61B 50/30 600/584 |

FOREIGN PATENT DOCUMENTS

| | | |
|---|---|---|
| JP | 2009-512858 A | 3/2009 |
| JP | 2010-502249 A | 1/2010 |
| JP | 2010-531169 A | 9/2010 |
| JP | 2013-522650 A | 6/2013 |
| TW | 476640 | 2/2002 |

(56) References Cited

FOREIGN PATENT DOCUMENTS

| TW | 476740 B | 2/2002 |
|----|----------|--------|
| WO | WO-2000/00233 A1 | 1/2000 |
| WO | WO-2000/65348 A2 | 11/2000 |
| WO | WO-2011119644 A1 | 9/2011 |
| WO | WO-2012019214 A1 | 2/2012 |
| WO | WO-2012/126507 A1 | 9/2012 |
| WO | WO-2013097899 A1 | 7/2013 |
| WO | WO-2013152087 A2 | 10/2013 |

OTHER PUBLICATIONS

Extended European Search Report issued in EP 17767708.5, dated Feb. 4, 2019 (8 pages).
International Search Report and Written Opinion issued by the U.S. Patent and Trademark Office as International Searching Authority in International Application No. PCT/US17/23246, dated Jul. 26, 2017 (17 pages).
Extended European Search Report issued in EP15834024.0, dated Mar. 13, 2018 (8 pages).

\* cited by examiner

Figure 1

100 - 199 - Fluid collection, containers and channeling

200 - 299 - Biosensors

300 - 399 - Microelectronics

400 - 499 - Software on microelectronics

500 - 599 - Devices for data visualisation and data handling

600 - 699 - Central services for handling of information

Platform overview

Visual detection - bottom/backside of menstrual pad

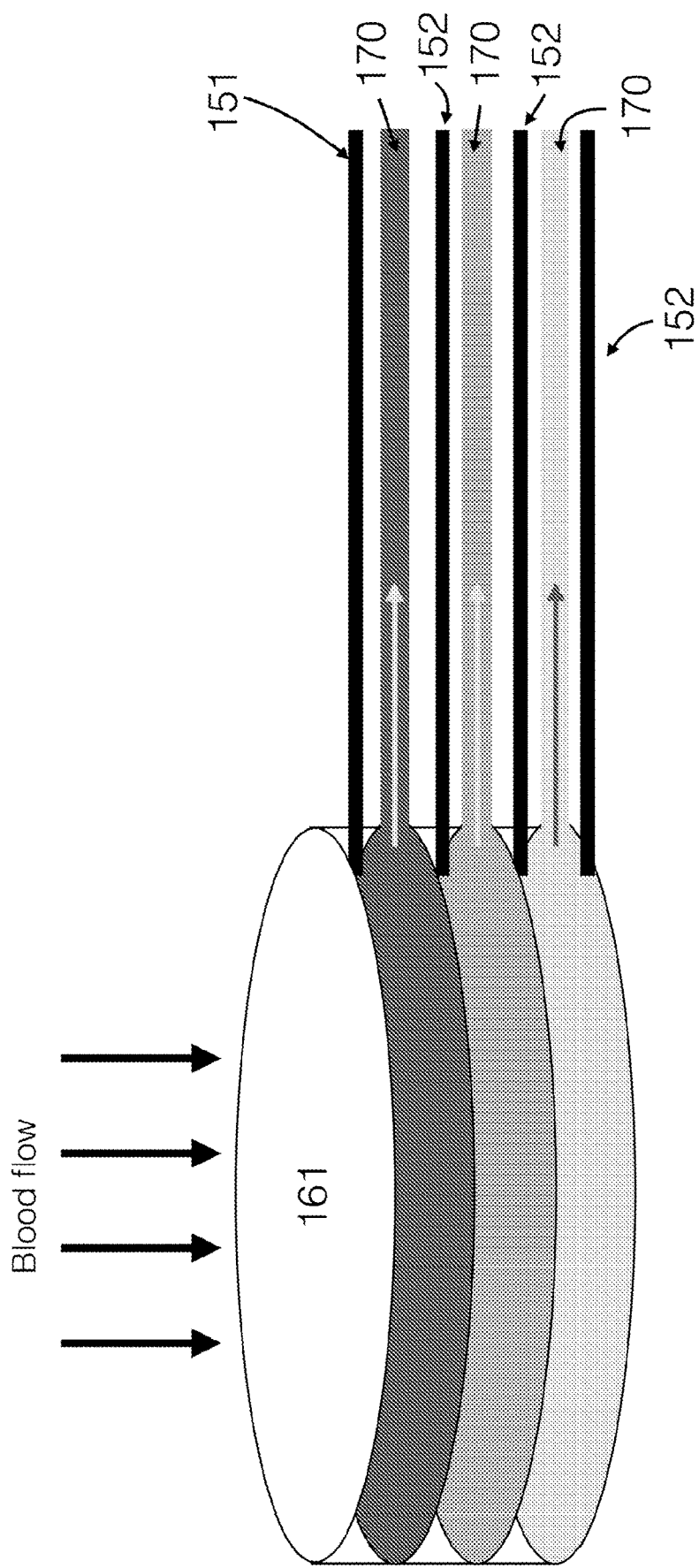

Fluid channeling example

Biochip example sideways

Fluid channeling example with timed delays

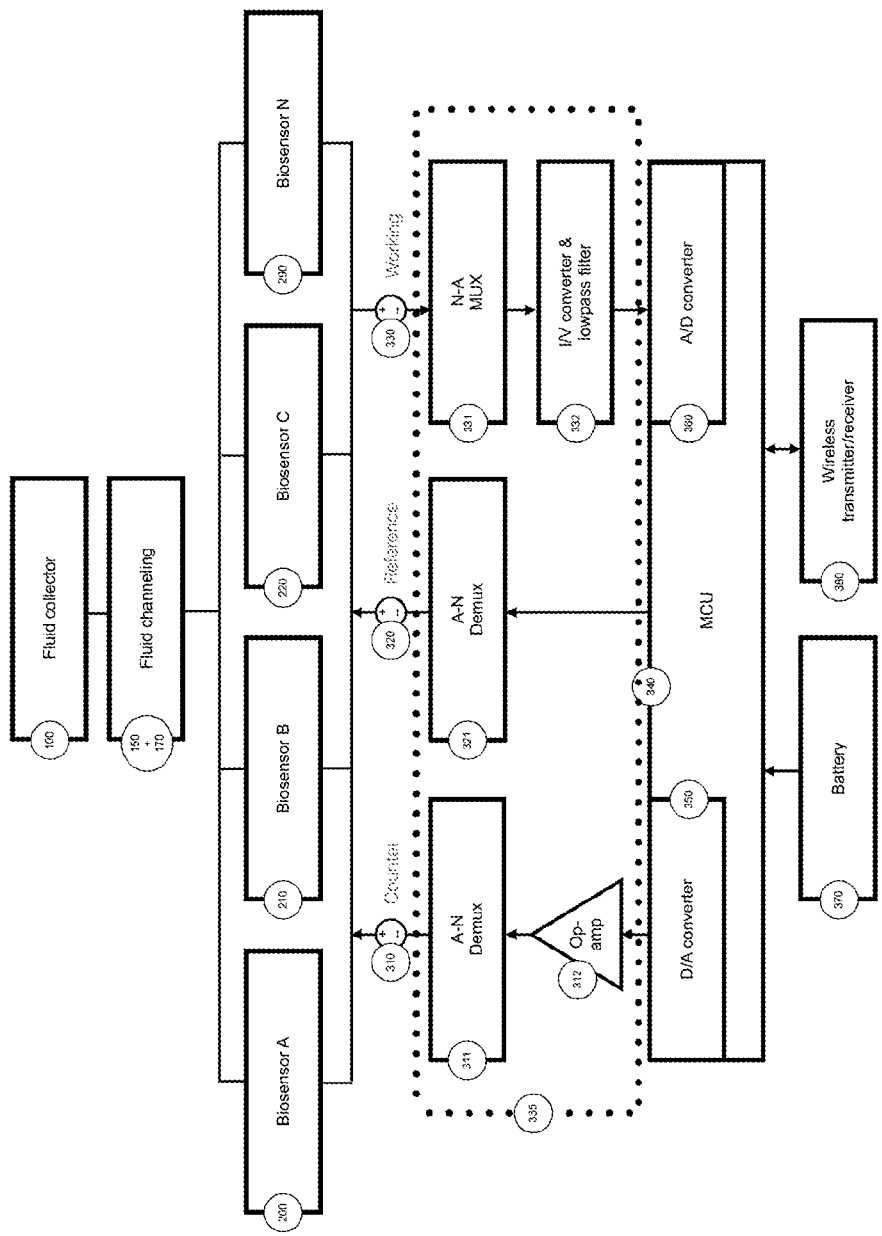

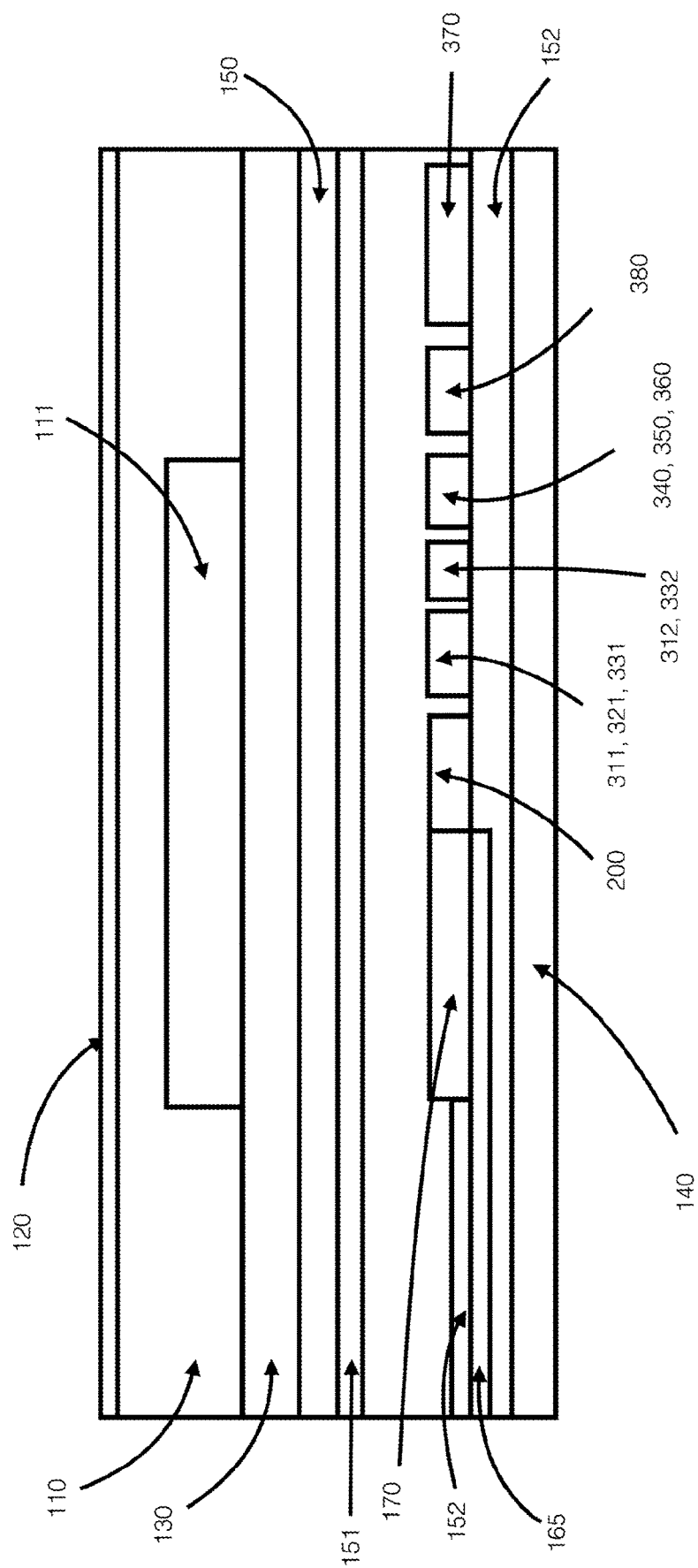

Biosensors connected with microelectronics

Electrochemical biosensor examples

Detection of DNA with an electrochemical DNA biosensor

Detection of antibodies with a scaffold biosensor.

Detection of cocaine or procaine with an electrochemical aptamer biosensor

Device handling

Pairing SMP and package of SMP with device and cloud-service

Figure 21
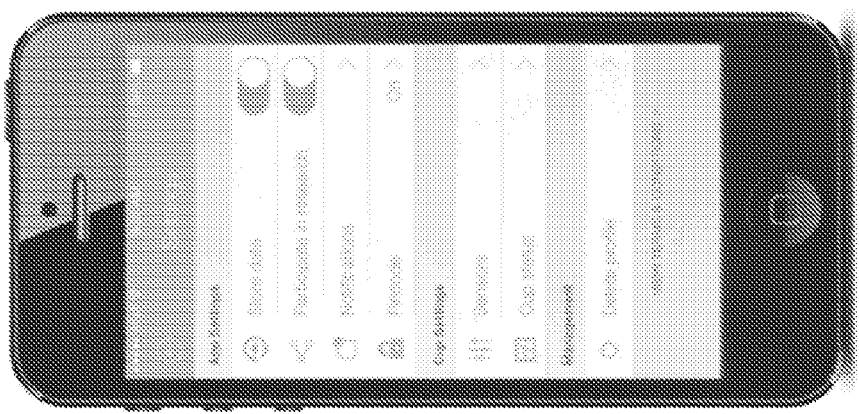
App settings
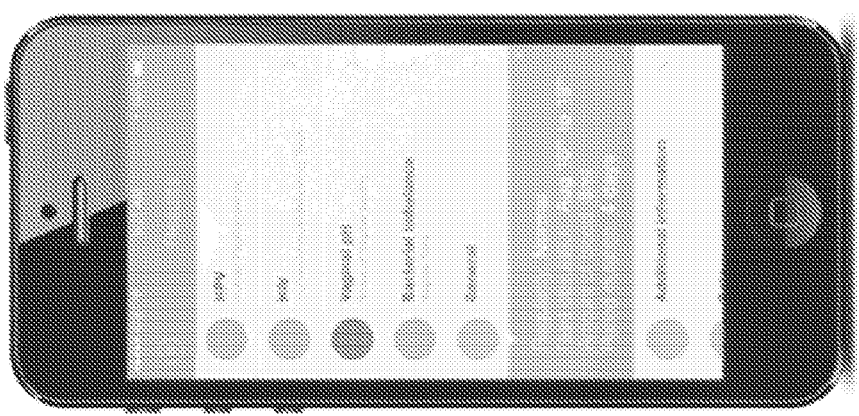
Application example
On/off of disease detection
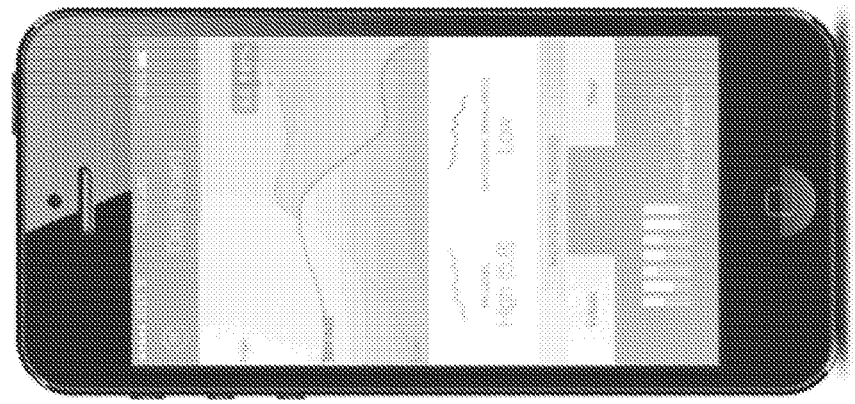
Graphs

SYSTEM AND METHOD FOR NON-INVASIVE ANALYSIS OF BODILY FLUIDS

REFERENCE TO RELATED APPLICATIONS

This application claims the benefit of priority under 35 U.S.C. § 119(e) to U.S. Application Ser. No. 62/040,341, filed Aug. 21, 2014, the contents of which are incorporated in their entirety by reference.

FIELD OF THE INVENTION

The present invention relates to feminine hygiene products, which enables health tracking and early diagnostics of a variety of diseases. The invention further relates to systems and methods for use in the collection and sensing of vaginally-discharged fluids.

BACKGROUND

Biomarkers or chemicals carried in the blood can provide significant health related information, which enables one to diagnose ailments, health status, toxins, performance, and other physiological attributes, even in advance of any physical signs. Determining the concentration of biomarkers such as electrolytes Interleukin-1a, Interleukin-1β, Interleukin-6, Tumor Necrosis Factor a, Interleukin-8, Vasoactive Intestinal Peptide, Neuropeptide Y, Substance P, Calcitonin-Gene-Related-Peptide, Orexin-A, as well as many other biomarkers, provides useful insights into the health of a test patient. For example, proinflammatory and anti-inflammatory cytokines as well as neurotransmitters such as neuropeptide-y are associated with many applications, including cardiac stress tests, stroke diagnosis, fatigue and post-traumatic-stress-disorder. Blood tests have been developed for all of these different biomarkers, however blood testing requires that blood is drawn and subsequently analyzed. As another example, direct measurement of electrolytes such as sodium and potassium provides an assessment of hydration. This is currently clinically diagnosed with a blood draw. For monitoring and diagnosing many medical conditions, blood is the most commonly used body fluid. However, collection of blood is an invasive procedure, which requires medical assistance. In addition many biomarkers (such as stress) can be influenced by the blood draw itself; patients typically have fear of being poked by needles, in addition to it being costly and inconvenient. As a consequence many conditions go undiagnosed, making treatment expensive, difficult and sometimes fatal. Other bodily fluids have also been considered for determining biomarkers in blood, for example, saliva, urine, feces, breath and sweat have all been considered, but are awkward and highly prone to contamination. Further, utilizing implantable sensors to analyze blood is expensive and invasive, and presents significant risks.

The medical industry is lacking a new innovative way of doing early diagnostics that is less costly, non-invasive and convenient yet reliable. This will enable proactive health care and prevent potential medical conditions from evolving.

Menstrual blood is recently known to carry these biomarkers. As it flows naturally from the body, collecting it provides an easy and non-invasive access to blood, without the need of invasive procedures, medical assistance or inconvenience for a user or patient.

Menstrual blood is a complex biological fluid composed of three distinct body fluids: systemic blood, vaginal fluid, and the cells and fluid of the late secretory phase of the uterine endometrial lining, which is shed during menstruation. Large-scale molecular proteomic studies of the composition of menstrual blood have shown considerable correlation with systemic blood; however, menstrual blood also contains additional fluids. Thus, at least 385 additional proteins can be detected in menstrual blood when compared with systemic blood. In 2012 the proteomics of menstrual blood was published and described several biomarkers for a wide range of disorders. These disorders include endometriosis, breast-, cervical-, ovarian- and endometrial cancer. Further studies have identified the HPV genome and other STDs such as *chlamydia* in vaginal discharged fluid.

Despite this, menstrual blood remains a fairly uninvestigated area for diagnostics. Analyzing menstrual blood for biomarkers raises various questions such as how can it be collected and tested, and how does the information on biomarkers obtainable from menstrual blood correlate to biomarkers found in the blood system and how this information is transferred to a person in a useful way.

SUMMARY

In one aspect, a new feminine hygiene product is provided that incorporates a biosensor, which renders it possible to utilize the beneficial properties of vaginal fluid blood with respect to health monitoring and diagnostics. The information is encrypted and transmitted wirelessly to a smartphone or other device for further data interpretation.

The inventions presented include a biosensor in the bottom layer of any female hygiene product including pads, tampons, panty liners and menstrual cups. The technology performs analysis on vaginal discharge to deliver valuable information to the woman about her health. The inventions provide the opportunity to use menstrual blood or other vaginal discharges as a convenient source of self-collected material that could be used for non-invasive health monitoring and diagnosis.

Such integrated diagnostics may have applications within various technical fields, e.g. medical devices, drug delivery and the technology could also be applied in stomas, blood bags/containers, catheters, IV kits, syringes, baby diapers, and condoms to do health analysis using other body fluids.

In one aspect, a vaginal fluid monitoring device includes an absorbent layer, wherein the absorbent layer is configured to be in proximity to flow of vaginal fluid; an electrochemical detection system configured to obtain data regarding at least one analyte in a vaginal fluid, said electrochemical detection system in fluid communication with the absorbent layer; and wherein the vaginal fluid monitoring device is configured to be coupled with a feminine hygiene product.

In another aspect, a fluid monitoring device includes an absorbent layer, wherein the absorbent layer is configured to be in proximity to flow of bodily fluid; an electrochemical detection system configured to obtain data regarding at least one analyte in a vaginal fluid, said electrochemical detection system in fluid communication with the absorbent layer; and wherein the bodily fluid monitoring device is configured to be coupled with a diaper or adult incontinence product.

In one or more embodiments, the electrochemical detection system includes a biosensor capable of generating a signal indicative of a property of an analyte; a microfluidic system for directing a vaginal fluid to the biosensor; and microelectronic circuitry for detecting and processing a signal generated by the biosensor.

In any preceding embodiment, the fluid monitoring device further includes a transceiver for wirelessly transmitting a processed signal from the electrochemical detection system.

In any preceding embodiment, the electrochemical detection system includes a biosensor capable of generating a signal indicative of a property of an analyte in fluidic communication with the absorbent layer; and microelectronic circuitry for detecting and processing a signal generated by the biosensor.

In any preceding embodiment, the fluid monitoring device further includes a collection layer disposed between the absorbent layer and the electrochemical detection system, the collection layer comprising one or more fluidic pathways for directing a vaginal fluid to the electrochemical detection system.

In any preceding embodiment, the fluid monitoring device further includes a fluid-impermeable layer disposed between the absorbent layer and the electrochemical detection system, said fluid-impermeable layer comprising at least one inlet in fluid communication with the absorbent layer.

In any preceding embodiment, one or more of the microfluidic system, biosensor and microelectronic circuitry are supported on a paper or plastic substrate.

In any preceding embodiment, the microfluidic system includes a plurality of microfluidic channels.

In any preceding embodiment, the plurality of microfluidic channels are configured to direct a vaginal fluid to a single biosensor.

In any preceding embodiment, the biosensor include a plurality of biosensors and each microfluidic channel is configured to direct a vaginal fluid to a different biosensor.

In any preceding embodiment, wherein the electrochemical detection system is configured to receive and analyze a plurality of samples.

In any preceding embodiment, the electrochemical detection system is configured to sequentially process a plurality of samples.

In any preceding embodiment, the biosensor comprises ligands capable of binding or chemically interacting with an analyte of interest.

In any preceding embodiment, the analyte is an nucleic acid, an antibody or a small molecule.

In any preceding embodiment, the electrochemical detection system includes electrodes in electrical communication with the biosensor, the electrodes configured to detect changes in current, impedance or voltages.

In any preceding embodiment, the device comprises computer readable instructions to encrypt data stored or transmitted from the electrochemical detection system.

In any preceding embodiment, the microelectronic circuitry is configured in an open circuit, wherein the circuit closes on contact with a vaginal fluid.

In any preceding embodiment, the feminine hygiene product is a pad or panty liner.

In any preceding embodiment, the pad or panty liner further includes a positioning element configured to maintain the absorbent layer in proximity to flow of vaginal fluid.

In another aspect, a method for analyte detection in a vaginal fluid includes providing a vaginal fluid monitoring device according to any of the preceding embodiments; collecting a vaginal fluid in the absorbent layer; directing the vaginal fluid into the electrochemical detection system; electrochemically analyzing the vaginal fluid in the electrochemical detection system; and wirelessly transmitting the information to a remote device.

In any preceding embodiment, the biosensor includes ligands that bind or chemically interact with an analyte of interest to cause a change of impedance or current or voltage.

In any preceding embodiment, the information is transferred by radio frequency (rf), Bluetooth, Bluetooth LE, NFC, GSM, CDMA, http, https or Wi-Fi.

In any preceding embodiment, there is a secure pairing between the vaginal fluidic monitoring device and the remote device.

In any preceding embodiment, the remote device is the cloud, a personal computer or smartphone.

BRIEF DESCRIPTION OF THE FIGURES

The present invention is described with reference to the following drawings, which are presented for the purpose of illustration only and are not intended to be limiting of the invention FIG. 1 is a chart of the various components of the invention according to one or more embodiments.

FIG. 6 is a schematic illustration of inlet and channeling of fluid through multiple vertical positioned channels according to one or more embodiments.

FIG. 10 is a schematic top plan view of one embodiment of the a system for collecting, electrochemically analyzing vaginally-discharged fluid and wirelessly transferring the information.

FIG. 11 is a cross-sectional view of the embodiment of FIG. 10.

FIG. 21 is a series of screens from an exemplary mobile device application according to one or more embodiments.

DETAILED DISCLOSURE

Figure 2:
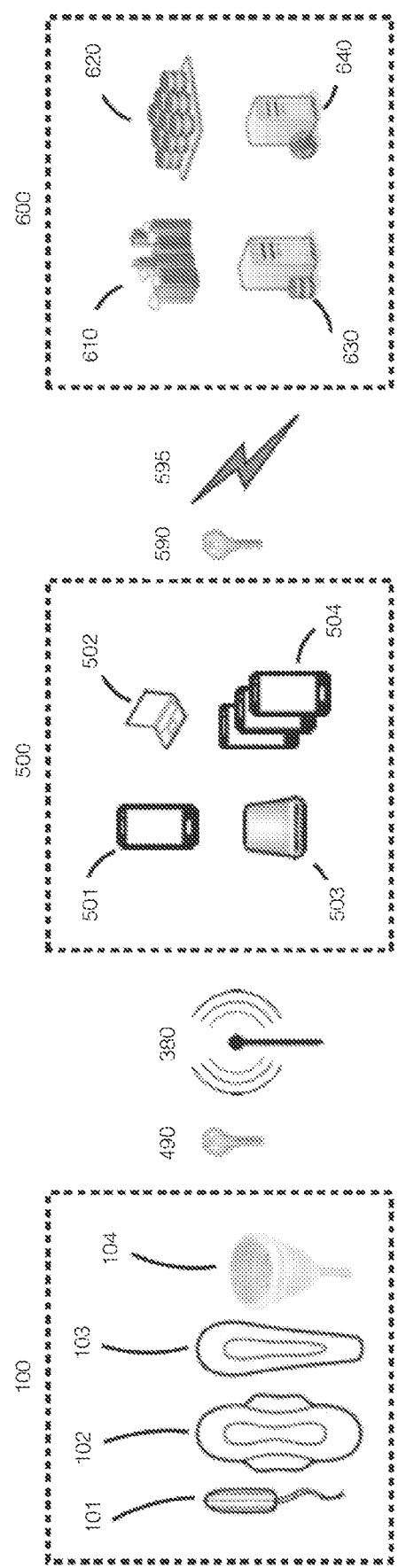
FIG. 2 illustrates a conceptual platform overview of the vaginal fluid collection, detection and analysis system according to one or more embodiments.

The present disclosure describes a new disposable feminine hygiene product (e.g., in the form of a pad, tampon, menstrual cup or similar structure), which embeds an electrochemical paper-fluidic platform as well as a microprocessor, battery and transceiver, hereinafter also referred to as an "the integrated diagnostic device," "vaginal fluid monitoring device" or "smart menstrual-pad" or "SMP." By analyzing e.g. fluids in biosensors, and converting the results into a digital signal through an electrochemical detection, specialized sensors analyzing bodily fluids (e.g., menstrual blood) can monitor the health and general well-being of a human. A non-limiting advantage of the integrated diagnostic device according to one or more embodiments is that the monitoring, analysis and reporting can be accomplished simply and with minimal steps and intervention by the patient. Once the feminine hygiene is positioned and the integral diagnostic has been activated, the process does not require further processing by the patient. As many people are uncomfortable handling blood or other bodily fluids, the ability to obtain health information in a clean and non-invasive manner is attractive.

The integrated feminine hygiene device provides for vaginal fluid collection using, for example, appropriately modified feminine hygiene products and integrated electrochemical paper-based microfluidics and microelectronics to provide the benefits of inexpensive, non-invasive, convenient and reliable health monitoring and diagnostics. As used herein vaginal fluid means biological fluids contained within or expelled from the vagina. While the discussion is directed to collection and analysis of menstrual fluids, e.g., the blood, cells and other bodily fluids shed during menses, vaginal fluid also includes vaginal discharges that are discharged during other times in a woman's menstrual cycle Another aspect of this invention is the collection of body fluids using diagnostic or healthy monitoring device integrated into e.g. a diaper or an adult incontinence pads. Although the structure and operation of the device is described with reference to feminine hygiene products and blood, it can find application in diaper or an adult incontinence pads and other bodily fluids.

To exemplify the fluid monitoring device, the following description is provided using menstrual pad, alternately referred to as a smart menstrual-pad (SMP); however, the features and operation is contemplated in a range of articles. The SMP allows analysis of menstrual blood biomarkers related to women's health and wireless transmission of encrypted health information to a smartphone. It is appreciated that the electrochemical paper-fluidic platform and supporting devices could also be integrated into other feminine hygiene products or with other devices for the collection of urine or feces that also could be used in the screening and testing for health conditions.

In one example, a woman using the SMP can establish a communication link between the vaginal fluid monitoring device and an electronic device (phone, tablet or other electronic device), for example, via a QR code or RFID sensor or other sensor, which is located on the fluid monitoring device or its packaging. The QR/RFID contains a unique ID (UID), which is readable by the electronic device.

Alternatively, the user can manually enter in the UID to an application, e.g., a mobile device application, that is designed to interact with the fluid monitoring device. This step is the first step of potentially a two-step verification of pairing an SMP to an electronic device. In a one-step verification, the UID is registered in the mobile device application and is now ready to be electronically paired with the SMB via a transmitter of e.g. Bluetooth, Bluetooth Low Energy (BLE), NFC or via other radio transmitting frequencies. Another way of transferring information from the SMP is to bypass 1-to-1 connection with a designated device. Implementing an e-SIM technology into the SMP and thereby replacing the transceiver, the SMP will have an embedded SIM-card solution build in to its hardware. Though GSM, CDMA or similar, the SMP can thereby communicate directly to a cloud service and transfer data directly over the mobile grid, just as a smartphone can today.

Further, if there are no devices available for the SMP to transfer its data to, the SMP can also connect securely to other surrounding devices 504 (see FIG. 2)—even without pairing through its UID. If the transceiver on the SMP detects a receiver from another unpaired device, and the device 504 is sharing an ID that can be recognized by the SMP as a device also running the designated app, the SMP can with encryption 490 offload its data, and route the information from the SMP directly in to the cloud-service 600 (or through other electronic devices, e.g., phones). Devices can also be paired with more than on SMP.

In a two-step verification system, the electronic device reads and identifies the UID (or the UID is manually entered into the application), and the application connects the mobile device to a cloud-server. The cloud-server has registered all UIDs, and also has a corresponding unique passcode associated to each UID, which is used as an encryption key. This passcode is securely transmitted to the mobile device via HTTP, HTTPS, GSM or similar method. Once the passcode has been received by the mobile device, the passcode functions as a lock providing an opportunity to view information, which can be sent to the SMP to effectively pair the SMP to the mobile device. A two-step verification service assures that only one device and one SMP are connected to each other, while also assuring that a cloud-server centrally knows what SMP and devices are connected.

If a device has only connected to a SMP through one-step verification, the device is not able to read the encrypted information from the SMP, but can only function as a routing system that securely uploads the data from the SMP to a cloud-service 610. This systems allows people without devices, to use the SMP, upload the information from the SMP to a cloud-service, and then access this information from any device connected to the Internet. To access the information from the SMP, the information to access this data may be written directly on the package of either one SMP or a package of multiple SMPs 710.

The user now receives a notification through the mobile device application, which asks for the Bluetooth or a similar transmitter/receiver to be turned on. This notification may be send to the user when s/he is scanning the QR code/RFID or it may be that the user will have to first activate the SMP in the app before a notification will be send. Either the users device automatically turns on its transceiver or she is asked via push notification from the designated app, to turn on the transceiver on her device which initiates the pairing with the SMP.

Once the Bluetooth is turned on, the device will search for SMPs within range. Only after the user starts using the SMP and thereby turns on a little micro battery, the Bluetooth on her device can receive data from the SMP.

In one embodiment, the micro battery is always turned on but needs to be wetted to send current through the electrodes, biosensor and MCU. In other embodiments, the battery is turned off but can be turned on in a number of ways. In one embodiment, the battery is turned on by connecting a small string from the package opening to the battery, which once the package is opened pulls out of the battery and functions as a switch to turn it on. This enables a long shelve life time as the battery will not be used even if it sits on the shelves for months or years. Alternatively the micro battery could be turned on by pushing a small button on the pad.

To further save battery lifetime, the pad can be configured so that it remains disconnected until first wetted with VF. The wetting of the pad closes an electrical circuit, which turns on the system allowing current to run from the battery through the electrodes to the biosensor and the MCU.

As soon as the battery is turned on it sends low amounts of current to the microprocessing central unit (MCU) and activates it. The MCU communicates with all three electrodes (counter electrode (CE), reference electrode (RE), working electrode (WE)) and also sends its UID through the transceiver looking for a Bluetooth device to pair with.

Figure 20:
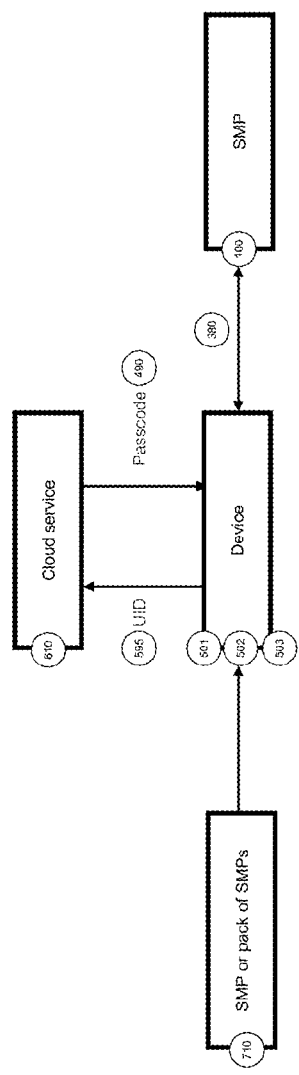
FIG. 20 is a flowchart illustrating the pairing or one SMP or a package of multiple SMPs to a mobile electronic device according to one or more embodiments.

As seen in FIG. 20, a flowchart is illustrated of how either one SMP or a package of multiple SMPs 710, is paired with a device 501, 502 or 503. To collect the UID from the package, the user first uses a device of e.g. a phone, to take either a picture of a QR code, scan an RFID or manually input the UID in to the app. The app then securely connects through HTTP, HTTPS or similar protocol 595 to a cloud service 610, from where in a central database 620, the UID is located and a corresponding passcode is sent back to the device. This passcode will then allow the device to read the encrypted data from the SMP, using the passcode to decrypt the information and visualize this in the app.

On the package 710, detailed information of how data from the SMP can be accessed without a single device, can also be written. This may be login-information to a cloud-service 610, where the user can access the information from the SMP from any device connected to the Internet.

Once paired, the results of an analysis from the SMP can be transmitted to the electronic device, which can also be transmitted to the cloud-server. The MCU may register a change in impedance and understand this indicates the targeted molecule is present. When it is ready, it can via e.g. Bluetooth, Bluetooth LE, NFC, GSM, Wi-Fi or similar, transfer either processed data or the raw data to the device or cloud server, which then reads and understands the raw data. This data may be preliminary test results from the biosensors, finished test results, timestamps associated with the tests and the software version running on the MCU. Depending on the processing power and battery capabilities, all processing of data could also happen in the MCU, however all raw data (e.g. current, voltage, timestamps etc.) will always be transferred and saved in the cloud-service.

As both the electronic device and the SMP are now looking for each other, they can if identified, share their unique information, and successfully conclude the pairing. Only a device from which the specific UID has already been read by the package, can successfully view data from the SMP. If the transceiver cannot find a device to pair with, it will go in to sleep mode. Once the users device and the SMP are paired the device can receive data from the transceiver.

If nothing (e.g., a signal generated by the targeted biomarker) is detected at this point the MCU may go to sleep mode. With regular intervals it wakes up and checks the electrical impedance by communicating with the CE, RE and WE.

Once the battery in the SMP system is powered on, it will send current through the MCU and wake it from sleep mode to awake mode. The MCU can now send current through the working electrodes to the biosensors. From the biosensor the current travels through a potetiostat/cheapstat which registers the current/impedance and sends this information to the MCU. The MCU will register if there is a change from the baseline and thereby understands if there is a presence of the targeted biomarker. When the MCU receives data from the biosensor, it always timestamps the information, encrypts it and saves it to NVRAM on the SMP.

The MCU then turns on the transceiver, which will start searching for a receiver, and at the same time broadcast its UID. If no reciever (the device it has paired with or any device with the app) is found the information is stored in the MCU and the MCU and transceiver goes to standby mode. Every e.g. 1, 5, 10 or 30 minutes the MCU wakes up the transceiver which then searches for the device it has been paired with or any other device with the app.

When a suitable receiver (device that has been paired with or device with suitable application) is located, it will off-load any data stored on the SMP to the device. This could be e.g. preliminary test results from the sensors, finished test results, timestamps associated with the tests and the software version running on the MCU. All data being transmitted is encrypted and can only be read by a device, if the device 501 or 502 has the corresponding passcode used to decrypt the data. This passcode is received by a cloud-service 610 initially as described earlier.

After off-loading its first data-package, the MCU will also check if there is any new software updates or processes that needs to be transferred from the device, either asked for by the device 501 or 502, or from the cloud-service 610. A software update could be updating the encryption algorithm, updating the time on the device, new information used to calibrate the biosensors, new or further tests to be run on the SMP, or other commands. Once this procedure has finished, the MCU has two options. To sleep again, activating a watch-dog service with commands and a plan for when to turn on again, to perform new activities, or to delete all data and let the battery run until it is empty.

If the SMP needs to perform additional actions, the MCU will go in to standby mode and turn on the watch-dog service. In intervals of e.g. 1, 5, 10 or 30 minutes, the MCU will then turn on again and see if there is any additional tests that could be performed on the biosensors. As the biosensors finish analysis, the MCU will offload data to either the device already paired with or to any other suitable device again with the potentially of receiving new commands.

Once all processes have been performed, the MCU commands the system to delete all data and to disable itself permanently.

As the woman menstruates, blood runs through the layers of the pad and reaches the microfluidic chip, which may be paper-based, silicon based or other. In the case of paper-based microfluidic chips, capillary force will direct vaginal discharge to specific locations where an electrochemical detection or measurement can take place. This causes a change in current or impedance. When the MCU "wakes up" and detects this change in current or impedance it sends a signal to the phone or other receiving device through the transceiver. If the phone is not near it will keep the information and go to sleep mode. As soon as a paired device is detected, the information is encrypted and sent to the device where it can be interpreted and displayed. Data can also be sent and stored in the cloud.

In the electrochemical paper-fluidic device, specific biomarkers (e.g. molecules, proteins, antibodies, antigens, DNA and mRNA, hormones, vitamins) or medication levels for chronical diseases will be analyzed and detected. This includes, but is not limited too:

Vitamins (e.g. vitamin D and B12), minerals (e.g. calcium, ferritin, iron, magnesium, phosphor, potassium, sodium), infectious diseases e.g. STDs (e.g. *chlamydia*, gonorrhea, herpes 2, HIV, syphilis, hr-HPV, trichomoniasis), fungi (e.g. *Candida albicans*), infection/inflammation (e.g. CRP, T-cell count, B-cell count), cardiovascular biomarkers (e.g. cholesterol, triglycerides, HDL, LDL,), cancer (e.g. cancer 125, cancer 15-3, 19, 9, 27-29, p16, fallopian tube cancer), fertility biomarkers (e.g. estrogen, FSH, LH, progesterone, GnHR), thyroid status (e.g. T3, T4), kidney biomarkers (e.g. creatinine, urea nitrogen), liver biomarkers (e.g. ALAT, ASAT), blood condition (e.g. hematocrit, hemoglobin, EPO, Hemoglobin A1C), drug management (e.g. warfarin, lithium, methotrexate, chemotherapeutics, digoxin, desipramine).

It may be that the microfluidic (paper-based or not) device will not be included in this solution and that the blood reaches the electrodes directly. In this case the electrode will be coated to detect a specific biomarker of interest which when the biomarker is present causes the change in current or impedance.

FIG. 1 provides a schematic overview of the menstrual or vaginal fluid monitoring device according to one or more embodiments. The device includes subsystems 100-199 for collection, containing and channeling vaginal discharge fluid (VF). These include VF absorbing products such as tampons 101, menstrual pads 102, panty liners 103 and menstrual cups 104 which may lead fluid 150 towards the bottom of the pads where it will be in direct contact with inlets 160. Multiple inlets 160 will lead the VF to a channeling device 150 such as a paper-fluidic system 170. The menstrual or vaginal fluid monitoring device also includes biosensors 200-299 for detecting biomarkers in the VF (e.g. antibodies, antigens (bacteria, viruses, parasites, fungus etc.), minerals, vitamins, lipids). Multiple biosensors may be embedded. The biosensors use electrochemical detection for identification and/or characterization of analytes in the menstrual or vaginal fluid. The menstrual or vaginal fluid monitoring device also includes a microelectronics unit (MCU) 300-399, which controls the system and transmits the data obtained from the biosensor. Software 400-499 and hardware 500-599 process data and provides data visualization and data handling. Optionally, central services 600-699 can be included for handling the information and data.

Methods for collecting and analyzing fluids and the type of biomarkers that can be detected are also described. An illustration of components in the platform can be found in FIG. 2 according to one or more embodiments. Feminine hygiene products with embedded biosensors and microelectronics 100 are illustrated in different formats, such as tampons 101, pads 102, panty liners 103 or menstrual cups 104. Once the biosensor has detected a certain biomarker the data will be encrypted 490 and transmitted securely 380 to the user's device 500 which may be a smart phone 501, computer 502, tablet 503, or other devices such as a smartwatch. Analysis of data received from the integrated diagnostic device, including interpretation, storage and tracking over time, can be carried out on an application stored on the mobile electronic device or a remote location.

The application receives data from the MCU and displays it in a user-friendly way on a device or in a browser window from a computer. The data could be a graphical illustration of biomarker level variations from month to month, also e.g. compared with the general populations level as shown in FIG. 21 in the first display. As shown in the second display of the same figure, this could also have an on/off illustration diseases (or other conditions, which are outside the normal value for the woman) and could indicate she should seek medical assistance. The application will also have a settings screen, which could include the profile of the woman (age, gender, height, weight, sexual activity levels etc.), shown on the third display on FIG. 21. The application could also suggest behavior changes to the user, where this advice will come from a mixture of data captured from the biosensors, but also other inputs generated by the user, from other sensors or sources. If a biomarker is detected that is critical to the health of the user, the app can also suggest the user to seek medical assistance from a doctor.

The mobile device application presents the user with values and text as well as graphical illustrations of how the levels of a certain biomarker or more is changing from month to month. The data from the SMP is being captured by the MCU, which through a potentiostat/cheapstat registers the change of impedance from a biosensor 1 (or 2 or 3 or n). From fabrication of the MCU, a data-set of reference baseline values of what normal values from a fluid-analysis looks like, is stored. For each biosensor, which has been programmed for a special detection pattern based on the analytic that the electrodes or paper fluidics has been coated with, will have a electrochemical recipe of what an electrochemical readout should look like on the biosensor. The electrical signals sent from the potentiostat/cheapstat read through a number of potential waveforms necessary to perform cyclic, square wave, linear sweep and anodic stripping voltammetry. To understand the raw data coming from the biosensors, the MCU has from fabrication reference data stored on its software, which is what is used as a baseline/background reference. If readout from the biosensor differs from the baseline/background reference data with current either increasing or decreasing, this will define both qualitatively if a target biomarker has been detected but also the quantities at which the target biomarker is present. It may be both qualitatively and quantitatively or only one of them depending on the target biomarker.

The information needed to understand and process the biosensor readout, can either be stored on the MCU 340, be read and understood by a device 501, 502 or 503, or even run as a calculation directly from a cloud-service 610.

After receiving this data, the MCU encrypts the information it receives from the different biosensors, and send the encrypted information to the users device. The device will be programmed to know what each biosensor detects and since it knows the encryption pattern it will be able to decrypt the information and translate the relative change in impedance from each biosensor to a concentration of a biomarker or simply detect that the biomarker is present. For example, the application can be programmed to recognize the presence of a biomarker for a sexually transmitted disease, e.g. STDs will be "present" or "not present," while the application can be programmed to calculate the concentration level of Vitamin D. In other embodiments, the data can be stored but may not be presented directly to the user. Depending on the specific biosensor the application may just notify the user with a "go see your doctor" type of message while other biomarkers may be "above normal" or "below normal". The app knows this because it will be comparing the data it receives from the MCU with the baseline/background reference data which is set in the software of the app or pulled down from the cloud or information received directly from the MCU 340. The application is also capable of storing, aggregating, comparing and displaying data over time. For example, the application is able to illustrate the biomarker variation from month to month. It may be that a biomarker will be able to measure levels of cholesterol and depending on lifestyle and diet the level will drop or increase. The app will be able to give advice based on the results and the desires of the user. An algorithm is programmed in the app, which will allow it based on biomarker values and potential information from the users profile or questions directly asked to the user which the user will answer in the app, to come up with intelligent suggestions to how the user may change behaviour to improve the users health. This information could be gathered from other app such as step tracking apps and the app could encourage the user to increase exercise based on e.g. steps taken during the last month and how this has affected certain biomarkers related to this type of exercise and health.

This could be integrated directly with exercise apps to track the level of activity and understand how this e.g. affects the users cholesterol. Cholesterol is just an example of a biomarker, which could be tracked monthly and which would change based on lifestyle.

In other embodiments, for example, when a device is not coupled to a feminine hygiene product 100, it is possible for other devices 504 to collect, but not read, the encrypted data and send it directly to a central data platform 600 where the individual or other users (e.g., medical health professionals) may login and view the information. In certain embodiments, the individual may be queried for permission to share the user's data 640 with the central data platform 600 for different purposes, e.g. science and research. Data can be encrypted 590 before it is sent 595 to the central data platform, which may be a cloud server 610, a database 620, a physical storage server in, e.g., hospitals or at the general practitioner 630.

Using encryption software embedded in the MCU, the data sent and received between the SMP and the electronic device, can be encrypted and decrypted before sharing shared via the transceiver. The unique passcode described in the two-step verification process, which is tied to the SMPs UID, functions as a key used by the device, to decrypt data sent from the SMP. Various types of encryption algorithms can be used, such as public-key algorithms like RSA and ElGamal mostly used by HTTPS for encrypting web communications. Symmetric-key algorithms like AES operated in CBC mode are popular for encrypting individual files can also be used. In a future embodiment of the solution, we envision using the blockchain technology known from bitcoin, to also serve as a secure network for handling data.

Figure 3:
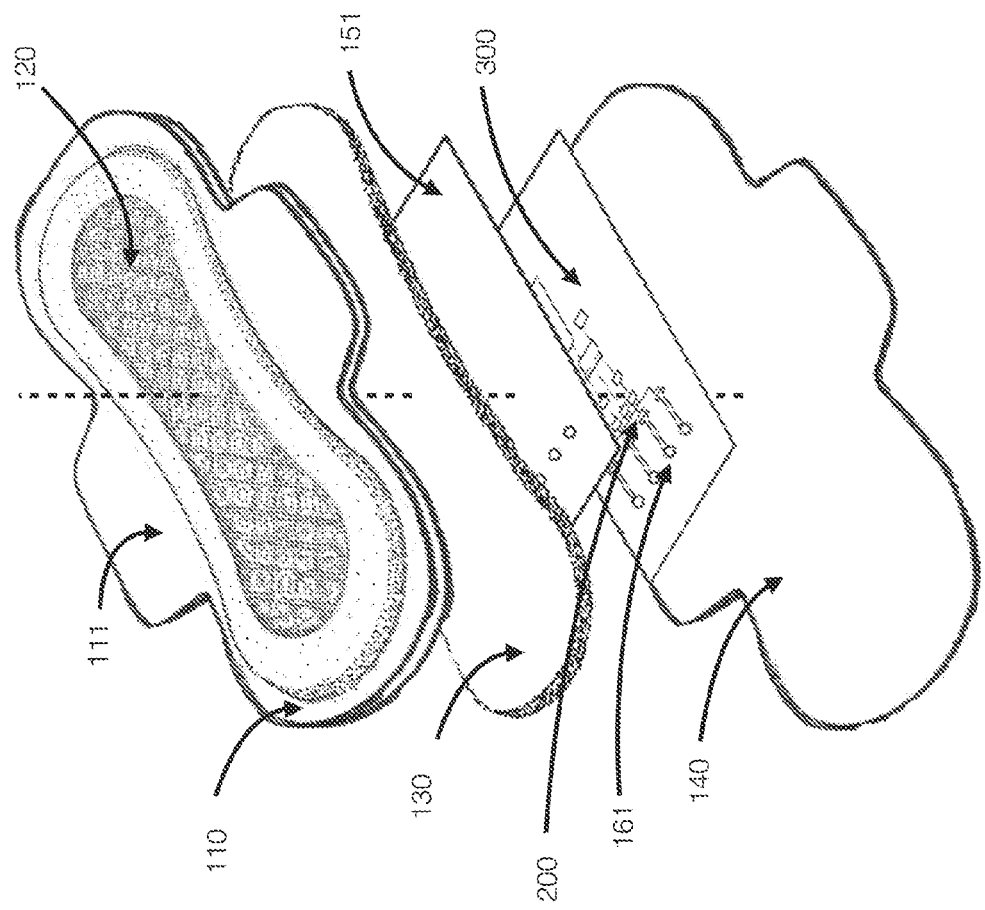
FIG. 3 is an exploded schematic illustrating the different layers of a menstrual pad (as an example of a fluid collector) according to one or more embodiments

The menstrual or vaginal fluid monitoring device includes an electrochemical detection system integrated into a feminine hygiene product. Because the biosensor is designed to use changes in an electrical state of the device, e.g., conductivity, voltage, current, impedance, etc., it is possible to conduct the detection and analysis remotely, e.g., without the need to handle the used feminine hygiene product. An example of a feminine hygiene product with embedded biosensors according to one or more embodiments is shown in FIG. 3. It illustrates the menstrual pad as an example but could also have been exemplified with tampons, panty liners, and menstrual cups. The figure illustrates the different layers of a menstrual pad (as an example of a VF collector 100). The VF is collected in the center 120 of the top layer of the pad 110, where the pad is highly absorbent of VF. The VF is collected in the second layer of the pad 130. Collection pad 130 may also include a filter or have a pore size that excludes particular components of the vaginal fluid from the biosensor. For example, pad 130 can be configured to exclude particulate matter or tissue. Pad 130 is in direct contact with a number of inlets, here illustrated with 4 inlets on a top protective layer 151, which seals the biosensor platform 200 as well as any microelectronics 300 embedded in the solution from the VF. There may be a channeling system (not shown) incorporated in pad 130 for channeling the fluid flow towards the inlets and the micro VF collector 161. In one or more embodiments, the microfluidic channels are a paper-based fluidic system. Only VF, which is absorbed by 161, will be directed towards the biosensor platform 200, e.g., via capillary force in the case of paper-based biosensors. The bottom layer 140 is a plastic layer that makes sure VF is kept inside the pad.

Figure 4:
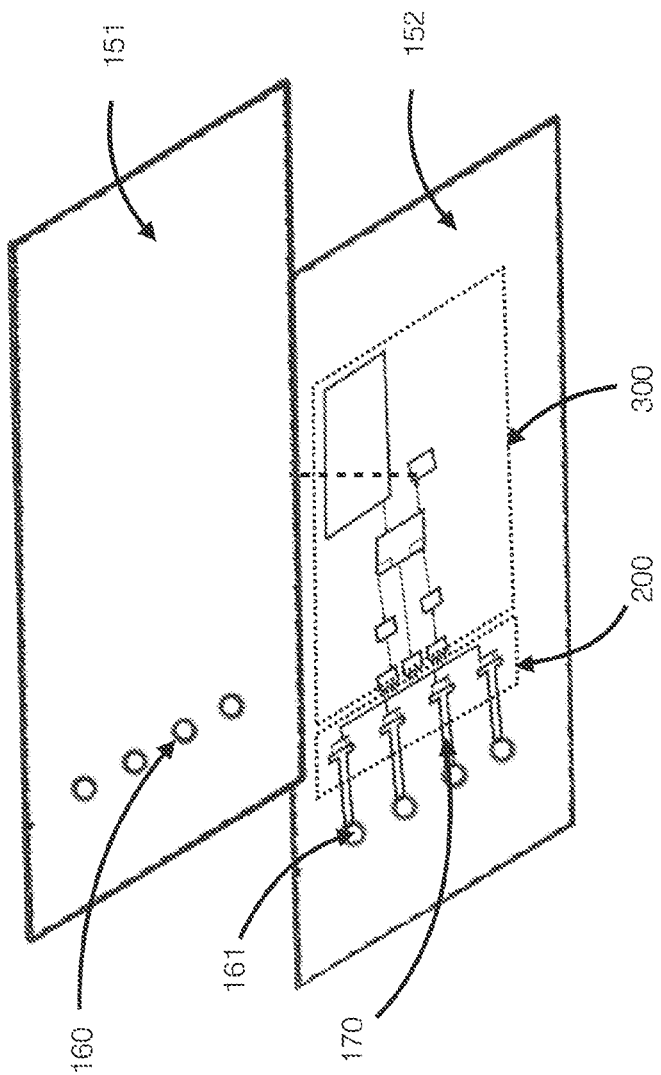
FIG. 4 is an exploded schematic illustration of a electrochemical detection system of the non-invasive medical diagnostic according to one or more embodiments

FIG. 4 is an exploded view of the electrochemical detection system, according to one or more embodiments. Underneath absorbent layer 120 and second layer of collection pad 130, is a protective layer 151 with inlet openings 160. The protective layer 151 is impermeable to fluids (could be a plastic or a hydrophobic material) and serves to protect the biosensor platform 200 as well as any embedded microelectronics 300. The inlet openings leads VF to the micro vaginal fluid collector 161 and then through a capillary fluid channeling system 170 to deliver the VF to the biosensor platform 200 for analysis. The inlets can be aligned next to each other, as shown here or on top of each other as shown in FIG. 6 or any other configuration. See, e.g., FIGS. 7A and 7B. Inlets can be of various sizes and shapes, e.g., circles, squares or rectangles.

Beneath the protective layer is a microfluidic system for fluid channeling towards the biosensor and microelectronics. The biosensor 200 and microelectronics 300 are mounted on a protective layer 152 on the bottom of the pad, which prevents the system to be in contact with VF that is in the bottom layer of the pad 140. In this way the biosensor platform and microelectronics, if these are embedded, are fully sealed in and not in unintentionally in contact with any VF, except the VF which has been absorbed through the inlets.

In one or more embodiments, the microfluidic system is based on a flexible platform. The flexibility accommodates the normal movements of the user when the feminine hygiene integrated device is worn. In one or more embodiments, the microfluidic device is a paper-based system. Paper-based microfluidic devices are a promising and cheap technology in developing analytical devices for point-of-care diagnosis. The paper-based microfluidics provides a novel system for fluid handling and fluid analysis, for a variety of applications including health diagnostics and monitoring, as well for other fields. Some of the reasons paper is an attractive substrate for making microfluidic systems include: it is ubiquitous and cheap, it is compatible with many chemical/biochemical/medical applications; and takes advantages of capillary forces for fluid flow, without the need of applying external forces such as pumps. Paper-based microfluidic system is low-cost, easy-to-use and disposable.

The microelectronics can also be mounted on a paper platform (or other flexible platform), positioned for interaction and communication with the biosensor. The electrical parts are becoming cheaper, lower powered, smaller in feature size and more advanced in their capabilities due to a shrinking of electronics, often down to a nano-scale resolution in features sizes, thus permitting their integration into the health monitoring diagnostics according to one or more embodiments.

Despite the physical sizes of components coming down to the millimeter size of Random-access memory (RAM) or Micro Controller Units (MCUs), the computational capabilities are still powerful enough to power the embedded software performing complicated algorithmic calculations. The downscale of electronics have enabled the rise of e.g. smartphones, connected wristwatches and other devices produced at the scale of hundreds of millions units.

This development has also led to radically downscaling in both size and price of potentiostats. Although potentiostats are the foundation of modern electrochemical research, they have seen relatively little application in resource poor settings. The main reason for the limited market success is their cost, as even the least expensive commercially available sell for thousands of dollars. An inexpensive electrochemical workstation such as a cheapstat powered by cheap and small electronics, can increase the access to electrochemistry-based analytical techniques for drug and health related monitoring. The cheapstat is an inexpensive, open-source (software and hardware), hand-held downscaled version of the potentiostat. This device supports a number of potential waveforms necessary to perform cyclic, square wave, linear sweep and anodic stripping voltammetry. It is suitable for a wide range of applications ranging from food- and drug-quality testing to rapid DNA detection.

FIG. 6 illustrates an alternative embodiment for positioning of inlets 160 (top of each other), here illustrated with a fluid channeling system 170. The inlet 160 in the protective layer 151 allows for direct contact between VF and the micro VF collector 161. The micro VF collector 161 can be formed from any suitable material which will readily transport vaginal fluid. Generally, a fibrous web, such as a cellulosic web and paper is particularly suitable for use in this application. The fibrous web can be treated with a hydrophilic substance which will promote fluid flow of vaginal fluid and coated with hydrophobic barriers (e.g., using wax printing) to prevent leakage and flow in unwanted areas and directions. As the fluid wets and is collected in micro VF collector 161, it travels through one or more channels 170 towards the biosensor 200 (not illustrated here). Each channel is separated by an impermeable layer 152 ensuring fluid only travels in a horizontal direction.

The fluid directing channels 170 may be made of same material as 161 but can also be coated with certain chemicals to filter or treat the VF in any way required to enable the detection of a certain biomarker once the fluid reaches the biosensor. The channels may also be build more advanced with multiple sections as shown in FIG. 8.

Figure 7B:
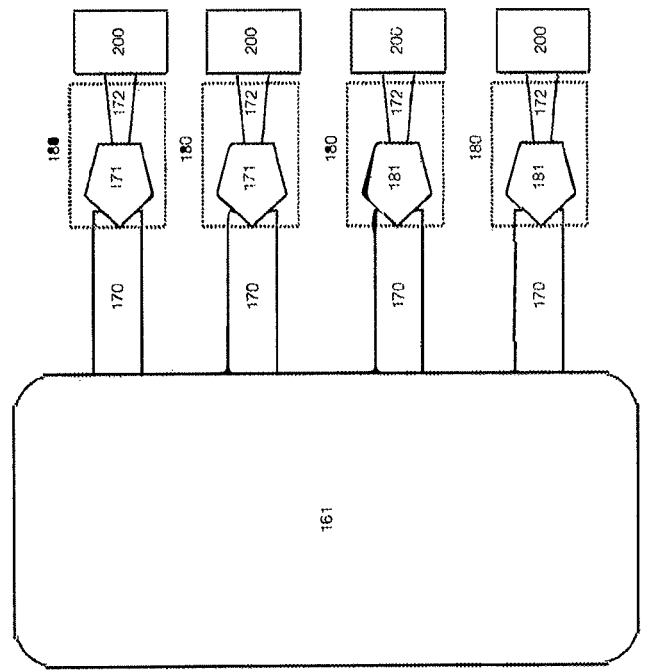
FIG. 7 A-B is a schematic top plan view of two possible embodiment of a channeling system for collecting and leading VF towards the biosensor platform using (A) radially and (B) laterally positions electrochemical detection system according to one or more embodiments.
Figure 7A:
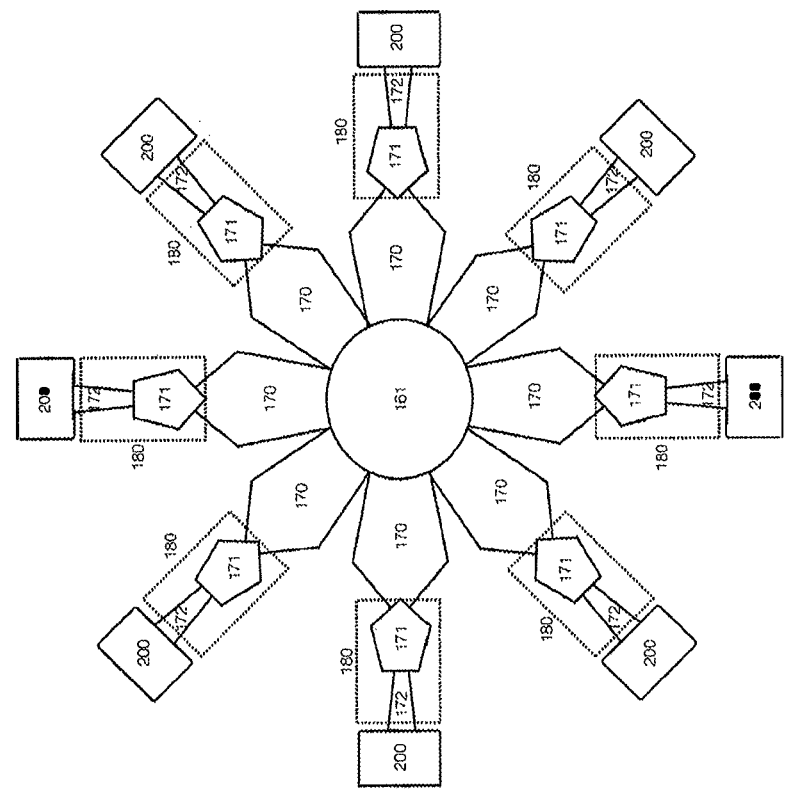
Figure 8:
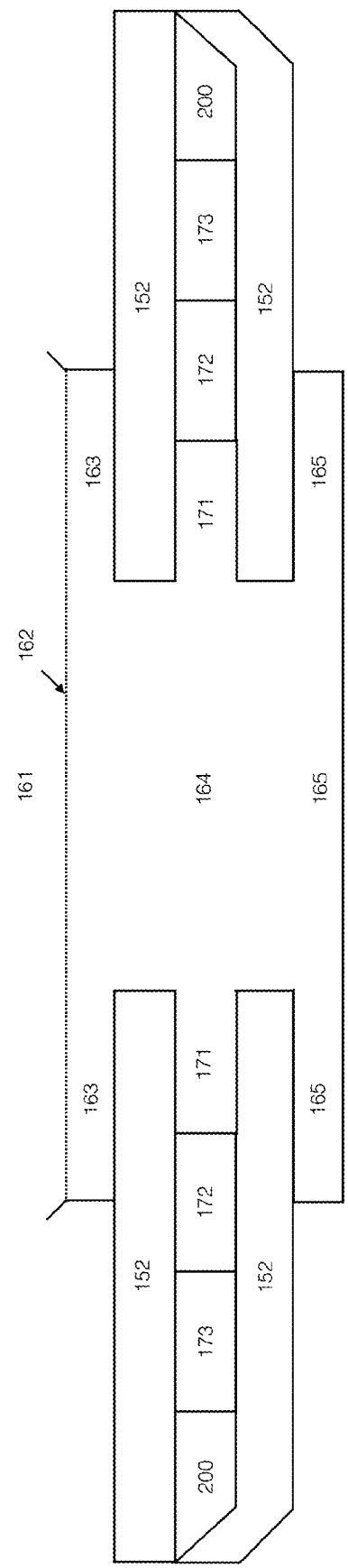
FIG. 8 illustrates a cross-sectional view of the embodiment of FIG. 7A.
Figure 9A:
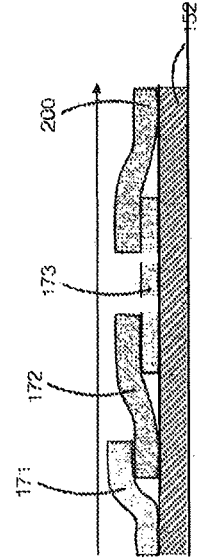
FIG. 9 A-E illustrates a cross-sectional views of a portion of an arm of the embodiment of FIGS. 7A and 7B showing channeling of fluid progressing through the arm over a period of time according to one or more embodiments.
Figure 9B:
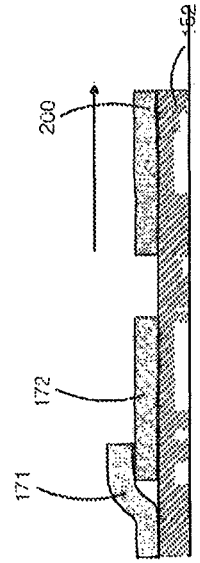
Figure 9D:
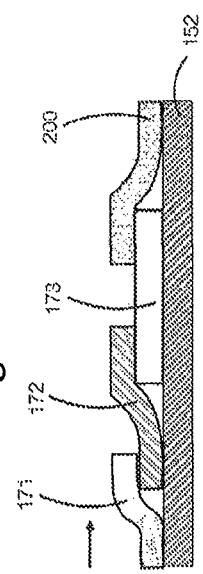
Figure 9E:
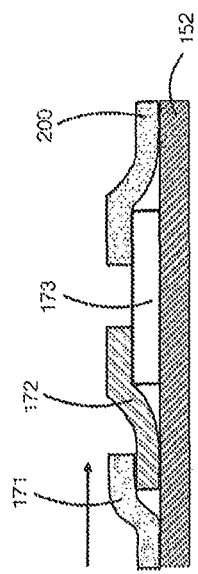
Figure 9C:
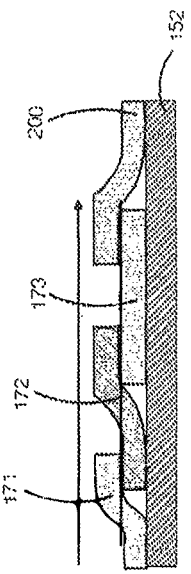

Illustrated in FIGS. 7 and 8 are a system which permit chronological VF absorption and storage of a plurality of samples. FIG. 7 is a schematic top plan view of a fluid distribution system to biosensor 200, while FIG. 8 shows a cross-sectional view of the same system. FIGS. 7A and 7B show two alternative arrangement of the component microfluidic elements.

The system includes a micro VF collector 161, which might have a VF membrane filter 162, that feeds VF into microfluidic channel 170. The VF membrane filter can filter plasma or a certain cell type or a protein. It can also be purification of the sample binding certain markers that create too much noise in the biosensor. In another embodiment the filter may be embedded be just before each of the 171 so that each "arm" has the potential to filter different biomarkers. Inlets 160 leads to the micro VF collector 161 which then leads to a VF collecting central base 163 which collects the filtered/unfiltered fluid and leads it to a central fluid transporting core 164, leading to a plurality of receiver elements 171. The central fluid transporting core 164 further leads to a lower fluid transporting VF dispatcher 165, which allows for VF storage and dispatchment therefore providing continuous fluid flow.

The micro VF collector member 161 can be formed from any suitable material which will readily transport VF. Generally, a fibrous web, such as a cellulosic web or paper is particularly suitable for use in this application. The fibrous web can be treated with a hydrophilic substance that can promote flow of VF. There could also be added/imprinted hydrophobic barriers onto 161 as well as 170 and 180 to prevent leakage of the VF. However, any material which will readily allow VF flow to be used as the VF collector member 161.

Separating the VF collecting central base 163 from the receiver element 171 is a liquid impervious flexible film 152 which has a central opening corresponding with the central fluid transporting core 164. Referring to FIG. 7A, radially extended receiver elements 171 are placed underneath the lower surface of this plastic film 152. Each arm leads to a VF transporting element 180, which consist of a volume delayer 172 and a volume regulator 173 which in turn extends radially outward to biosensor 200. FIG. 7B shows similar elements in which the microfluidic channels 170 and VF transporting elements 180 are located on one side of F collector member 161. The VF receiver 171, VF transfer element 180, VF biosensor 200, are all resting on the upper layer of another liquid impervious flexible film 152. In other embodiments, multiple arms consisting of 171, 180 and 200 can be placed on top of each other, each separated with a plastic film such as 152 as this would allow for more biomarkers to be analyzed.

The VF delayer 172 acts to delay fluid flow to the biosensor 200. Each delayer 172 is slightly different from all other delayers. Each of the different delayers delays the fluid flow for a different period of time so that the VF reaches each of the collection pads at different times, thereby providing discrete chronological VF samples at different times, here shown with 8 times being exemplary only and non-limiting. The delayer 172 can be formed from a variety of different materials. One particular material suited for this application is a water soluble polymeric film member which inhibits fluid flow but gradually dissolves in the presence of a fluid like VF. Once it dissolves, it permits VF to flow past the delayer to fill the volume regulator 173 and the biosensor 200. The different delayers 172 can be formed from different thicknesses of the water soluble film or the polymeric composition of the film can be adjusted in each of the gates to establish different dissolution rates. This can be done for example by choosing film with different molecular weights. One preferred material is polyethylene oxide. The solubility of these films can be adjusted by changing the molecular weight of the polyethylene oxide with the lower molecular weight films being more soluble. Alternately, the thickness of the film can be adjusted, with a thinner film being dissolved more quickly than a thicker film. Once the delayer 172 dissolves, the VF will pass. The delayer 172 may fully dissolve, or it may simply become VF permeable, achieved for instance with a cloth or cellulose fiber film that has been embedded with polyethylene oxide polymer. The delayers 172 are in turn in fluid communication with what are referred to as volume regulators 173. The volume regulators 173 are simply fluid conduits that only allow fluid flow for a limited period of time before they become suitably impervious to fluid flow or solute diffusion. These fluid conduits will allow VF from the delayers to flow to the biosensors 200. However after a certain volume of VF has passed through the volume regulator 173, it will dissolve or become impermeable to further fluid flow or solute transport, interrupting the fluid path, and preventing further VF solutes (ions, molecules, biomarkers) from being transported into or out of the analyzer. Thus each analyzer would receive VF sample at a time permitted by the delayer 172. When the volume regulator 173 dissolves, it isolates the sample on the biosensor such that the biomarker information is not blended, diluted, or distorted by VF from later collection time periods. The present invention includes all methods that achieve this same basic functionality of sampling and isolating VF samples, storing them in a manner that properly preserves them, and sampling and storing them in a manner which the VF sample is representative of the VF excreted at or near the time of sampling. The VF collection and analyzing system in FIGS. 7 and 8 can therefore utilize alternate materials that physically or chemically change in any manner that provides similar results, including but not limited to bridges made of polymers that cross-link after some time of VF exposure to prevent fluid flow and/or gates based on a material that slowly swells and moves into fluid connection with the next fluidic component of a VF collector.

The volume regulator 173 can be any VF soluble member that has an acceptable dissolution rate. In particular, the bridge can be a polyethylene oxide thread having a fibrous surface which allows capillary migration of the VF across a polyethylene thread. Once the thread dissolves, fluid will no longer pass to the biosensor 200 as there will be a void on the upper surface of the plastic film 152 thereby preventing further fluid flow.

The core central fluid transporting core 164 extends through the system leading to an lower fluid transporting VF dispatcher 165 which simply allows fluid flow promoting the continued migration of VF through the collection member 161. The lower fluid transporting VF dispatcher 165 can further be coated with a super absorbent hydrogel (not shown) to further facilitate fluid flow.

FIGS. 9A-9E illustrate in a cross-sectional view of a portion of an arm of the embodiment of FIG. 7, showing fluid progressing through the arm over a period of time. VF, shown as stippling, will travel up the central fluid transporting core 164 extending to the receiver element 171 (see FIG. 9A) and then to the delayer 172, which allows the VF to reach biosensor 200 at different times. (see FIG. 9B). The delayer 172 can be of different lengths or sizes so that the time for flow of VF from receiver element 171 to the volume control element 173 is delayed by different times. Volume control element 173 controls the volume of liquid to pass to biosensor 200. A first volume control element 173 will dissolve at time T1 and a second at time T2 and third at time T3 and so on, so that the fluid flow can continue for different times and thus allow differing volumes of liquid to flow to the biosensor 200 (see FIG. 9C). The fiber volume regulator 173 will allow VF to immediately migrate to the respective biosensor 200 (See FIG. 9C). After a period of time, the volume regulator 173 will dissolve (see FIG. 9E), because the volume regulator is narrow and breaks up by capillary-breakup, there is none or not enough polymer to allow VF to continue to the biosensor 200. Thus, a first biosensor will stop collecting VF at time T1+X, and a second at T2+X, and a third at T3+X, and so on, with X being the time required for the volume regulator to dissolve. The time X could also be a variable controlled, especially so if time-averaged sampling is desired.

Various components of the menstrual blood collection and analyzing system shown in FIGS. 7 and 8 can be arranged in multiple ways, some elements might even be excluded, so long as they satisfy the operating principles of the present invention. In use, the time specific menstrual blood collection and analyzing systems shown in FIGS. 7 and 8 are applied by placing them in feminine hygiene products. Components of multiple 200-systems may be stacked and connected with additional bridges or gates to increase the duration of use and total sample collections. Furthermore, this type of system, may also prove useful for simple chronological collection and storage of other fluids, ranging from saliva to urine or other biological and non-biological fluids. The biosensor 200 can test for a variety of different biomarkers. In particular it may be desirable to analyze one or more reference biomarkers to determine the amount of a reference biomarker and compare this to a non-referenced tested biomarker, where the concentration of the referenced biomarker is generally known. This permits one to use the ratio of the referenced biomarker to the tested biomarker to determine the concentration of the tested biomarker without knowing the volume of VF being tested. Typical reference biomarkers include known methods such as those used to determine electrolyte balance. Some biomarkers found in VF may degrade quickly due to enzymatic or other forms of decomposition or breakdown, and storage, preservation, chemical reacting, or other chemicals, materials, or components, may be included in the biosensor 200 to preserve the desired information provided by the biomarkers. For different biosensors see discussion of FIGS. 13-18, below.

Electrochemical analysis is ubiquitous in analytical laboratories but it usually utilizes complicated and expensive instruments, which requires special trained technicians. However for use in lower-developed countries, in the field or in the home-care, there remains a need for analytical devices that are inexpensive, disposable, portable and easy to use. Electrochemical paper based analytical devices as well as screen printed electrodes, have recently been explored as the basis for low-cost, portable devices, especially for use at the point of care. They generally employ a printed Ag/AgCl pseudo-reference electrode, but other types materials has been used to produce the electrode, often coating it for a specific reaction. Another type of biosensor referred to as E-DNA sensors perform well even when exposed directly to blood. E-DNA allows for quantitative, reagentless, electrochemical detection of nucleic acids (DNA, RNA), proteins (including antibodies) and small molecules analyte, directly in unprocessed clinical samples. Such paper based or flexible platforms can be used to screen for a large number of disease states and conditions.

Figure 12:
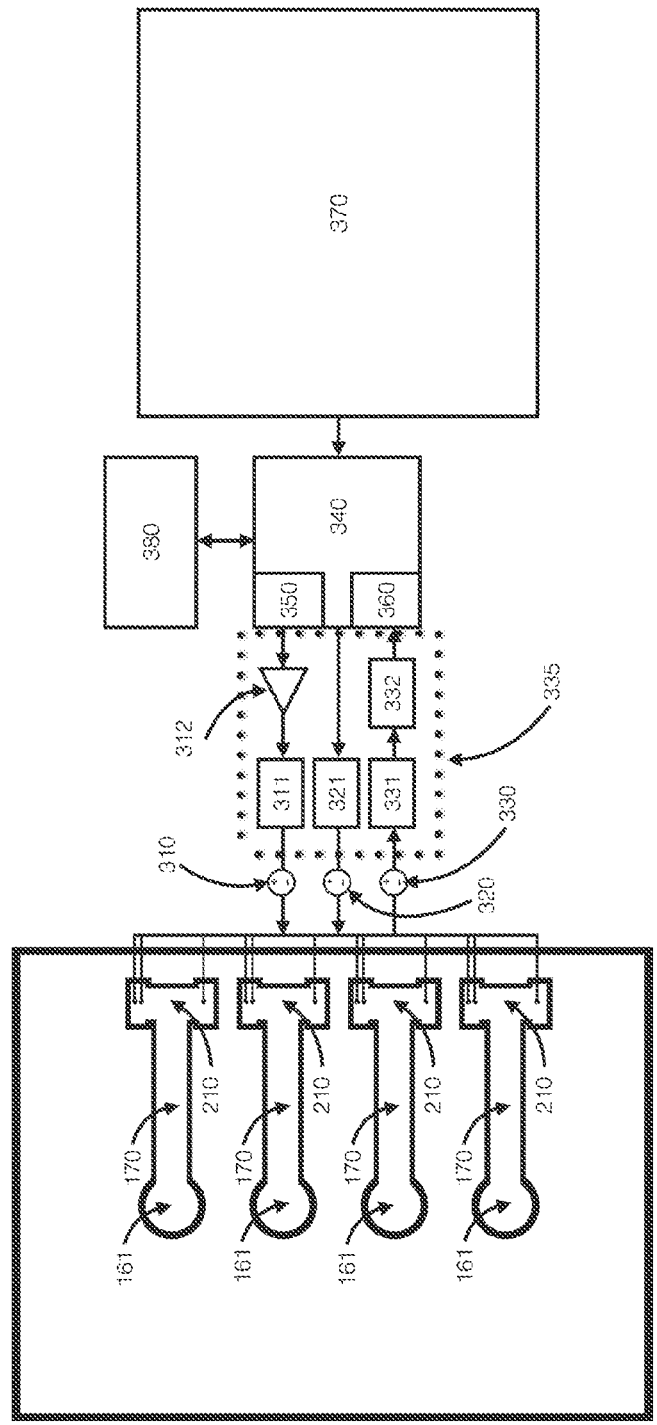
FIG. 12 illustrates biosensors connected with microelectronics according to one or more embodiments.
Figure 13A:
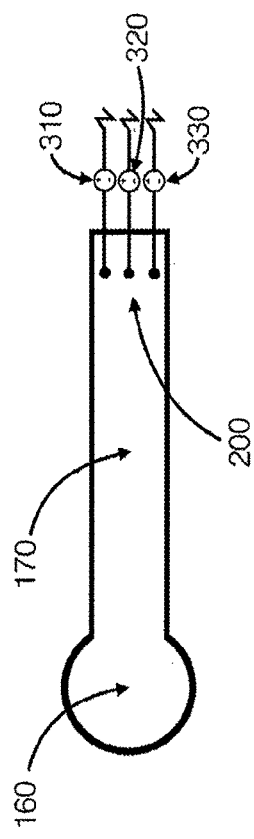
FIG. 13 A-D illustrates electrochemical biosensor that can be used in the electrochemical detection system according to one or more embodiments.
Figure 13B:
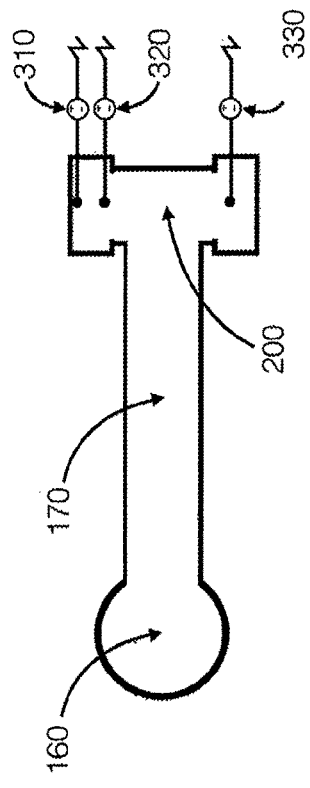
Figure 13D:
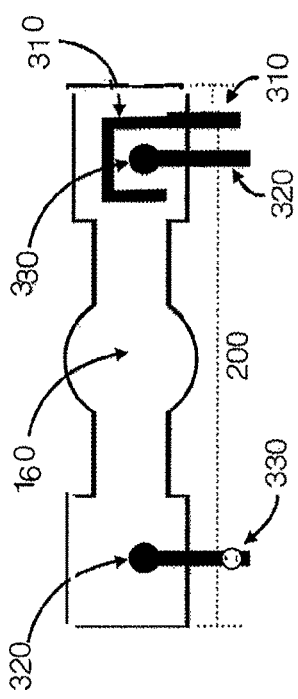
Figure 13C:
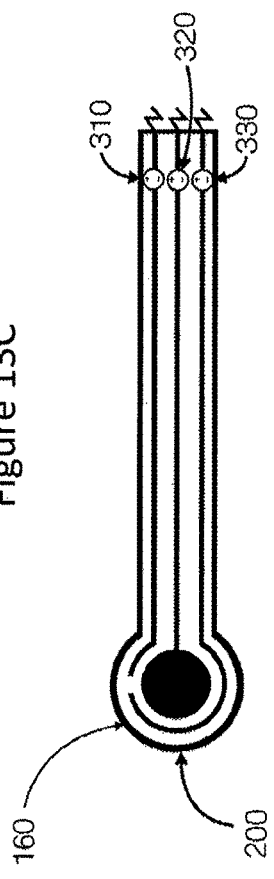

A system overview for collecting and electrochemically analyzing vaginally-discharged fluids (VF), such as menstrual blood (MB), and wirelessly transmitting the information to a device 500 such as an smartphone 501, is shown schematically in FIG. 10. The actual system embedded in a menstrual pad is shown in cross-sectional view in FIG. 11. A schematic illustration of the electrochemical detection system is further illustrated in FIG. 12.

Referring to FIGS. 10 and 11, the top layer of a pad 110, which includes a highly absorbing layer 120 and potentially sticky wings 111, is where the VF will be absorbed. Underneath collecting pad 130 is a fluid channeling system 150 which leads the VF towards the protective layer 151. This layer 151 protects the biosensor 200 and microelectronic 300 platform from being in direct contact with the VF. In the protective layer is multiple inlets 160 which allows VF to enter. Through a channeling system 170 VF is directed to multiple sites where different biosensors 200 are located. The biosensors are coated with specific molecules, which enables detection of specific biomarkers from the VF. It can be either the paper itself, which is coated, or the electrodes which gives the potential to exclude the paper-fluidic from the system. The biosensor 200 may be an electrochemical paper-based microfluidic sensor or an electrochemical DNA biosensor or another kind of biosensor.

Each biosensor is coupled to three sensing electrodes: a counter electrode 310, reference electrode 320 and a working electrode 330. The Multiple configurations of biosensors with electrochemical detection is shown in FIG. 10013. All counter electrodes from each biosensor runs through a demultiplexer (A-N demux) 311 while all reference electrodes runs through another A-N demux 321. Finally all working electrodes from the biosensors run through a multiplexer (N-A mux) 331. The electrochemical detection biosensor and associated electrodes are shown in FIG. 13. A battery 370 sends current through a D/A converter 350. The current then runs through an Op-amp 312 and through the counter electrodes 310 which sends current through the VF and the working electrode 330 to a IV converter and lowpass filter 332 to the A/D converter 360 and finally the MCU 340. The reference electrode 320 has a known reduction potential and its only role is to act as reference in measuring and controlling the working electrode's potential and at no point does it pass any current. These three electrodes make up the modern three electrode system. Binding one or more biomarkers from the VF in one or more of the biosensors 200 causes a change in the impedance or current in the working electrode 230. This will either increase or decrease the current detected by the MCU 340. The relative change in current relates to the amount of biomarker detected at that specific biosensor 200. This information/data is stored in the MCU 340, encrypted 490 and finally send to a device 500 e.g. a smart phone 501 through a wireless transmitter/receiver 380.

The MCU received data (e.g., processed signal data) from the potentiostat and uses embedded software compare changes in e.g., electric impedance to a reference condition. An example of such an MCU can be bought from companies such as ARM or Intel or Texas Instruments.

The MCU is programmed to sleep with a specific time interval and to it wake up to run a test. If the impedance detected in the system has not changed, it will sleep again and wake up after another time interval. If it detects a change and therefore the targeted biomarker, it will encrypt both raw data and processed data and send the information to the device once the device is near. If the device is not near for it to transmit it will hold the information. Once the device comes near the information is send to the device.

Figure 14:
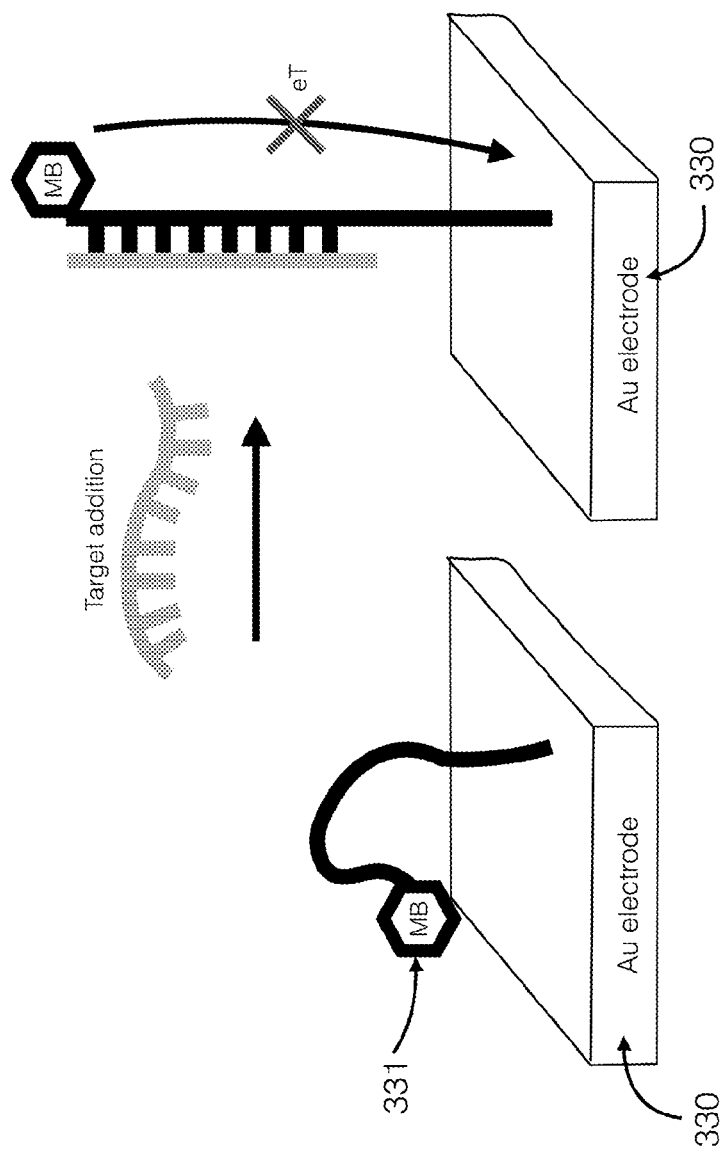
FIG. 14 is a schematic illustration of detection of DNA with an electrochemical DNA biosensor according to one or more embodiments.

Once the phone receives the data in the mobile device application, it will display information in a such manner that the woman can read the results. Some information may only be displayed as "you should consult your doctor". The phone also sends the information to the cloud for storage. Optionally, it can potentially be shared with $3^{rd}$ parties e.g. for research or similar (after approval from the woman). The sharing of her data can be done anonymously. The phone sends the information to the cloud through via http or https The electrochemical detection biosensor and microelectronic platform which is schematically shown in FIG. 10 is also illustrated with correct locations in FIG. 13. Any biosensor that detects the presence or amount of an analyte or biomarker using electrochemical principles can be used according to one or more embodiments. An illustration of an electrochemical DNA biosensor (E-DNA biosensor) is shown in FIG. 14. In this case the working electrode 330 is made of gold and coated with a specific DNA sequence 331 which is complementary to the target DNA one wants to detect in the VF. Binding of the target to the E-DNA biosensor changes the efficiency of the electron transfer to the electrode, thereby altering e.g., the impedance of the electrical circuit.

Firstly the nucleotide probe strand 331 is affixed to a gold electrode 330. The probe has been chemically modified during synthesis by the addition of a C6 thiol at its 3'-end and a redox-active methylene blue (MB) at its 5'-end. The addition of a C6 thiol at its 3'-end ensures a mono-self-assembled layer of the probe strand 331 onto the gold electrode 330. By attaching modified probe DNA 331 to the working electrode 330, the electrode has been prepared to react with a specific DNA sequence found in VF. Binding of the target to the E-DNA biosensor changes the efficiency of the electron transfer to the electrode, thereby altering e.g., the impedance of the electrical circuit. The working electrode 330 is connected to a potentiostat 335 (e.g. a cheapstat) together with a platinum counter electrode 310 and silver/silver chloride reference electrode 320. The potentiostat maintains the potential of the working electrode at a constant level with respect to reference electrode by adjusting the current at an auxiliary electrode. The background peak-performance impedance will at fabrication be known using square wave measurement from 0 to −0.6 V typically with amplitude of 25 mV and a step size of 1 mV. The optimal square wave frequency will depend on the details of the probe architecture. The electrodes are placed at the end of the fluid channel 170, which channels the VF towards the electrodes. Once the VF which contains the target DNA molecule of interest, the E-DNA will in a typical timeframe of 5 to 120 min depending on the size, structure and concentration, register the target DNA which will result in a change in impedance in the second square wave voltammagram measured by the potentiostat 335. The height of the peak at typically −0.35 V will change from the initial, background measurement measured in the sensor preparation. The magnitude of this change is related to the concentration of the analyte. It is the main output data of this sensor.

Figure 15:
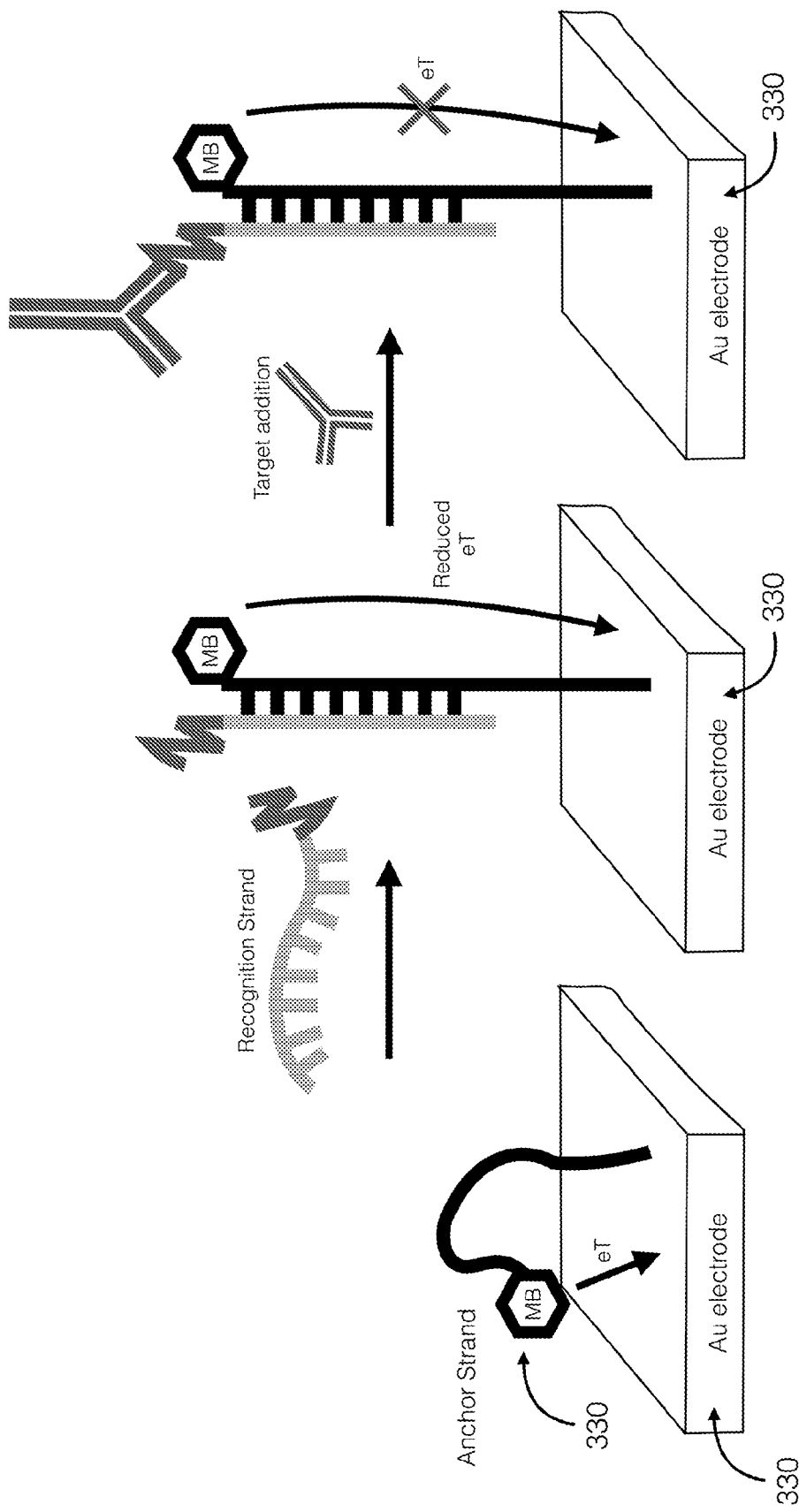
FIG. 15 is a schematic illustration of detection of detection of antibodies with a scaffold biosensor according to one or more embodiments.

E-DNA can also be used as an antigen/antibody detection as illustrated in FIG. 15. In this case the methylene-blue and thiol-modified DNA probe which has been assemble on to the working gold electrode 330, mainly serves as an "anchor" strand. It is attached directly to the gold electrode 330 and then it is hybridized with a second, recognition DNA strand 333 that has been covalently conjugated to the relevant antigen. Binding of the target to the E-DNA biosensor changes the efficiency of the electron transfer to the electrode, thereby altering e.g., the impedance of the electrical circuit. Again the modified working electrode 330 is connected to a potentiostat together with a platinum counter electrode 310 and silver/silver chloride reference electrode 320. When fabricating these E-DNA biosensors a background square wave voltammetry is performed using same principle described for FIG. 14. This background measurement will be converted and read by the potentiostat 335 and registered and saved in the MCU 340. This enables the MCU to register the change the current relative to this background measurement when the target molecule binds to the E-DNA. When VF reaches the E-DNA biosensor, and if the target antibody is present, the peak at the same voltage will decrease which is measured by the potentiostat and registered by the MCU. The magnitude of this change is related to the antibody concentration.

Figure 16:
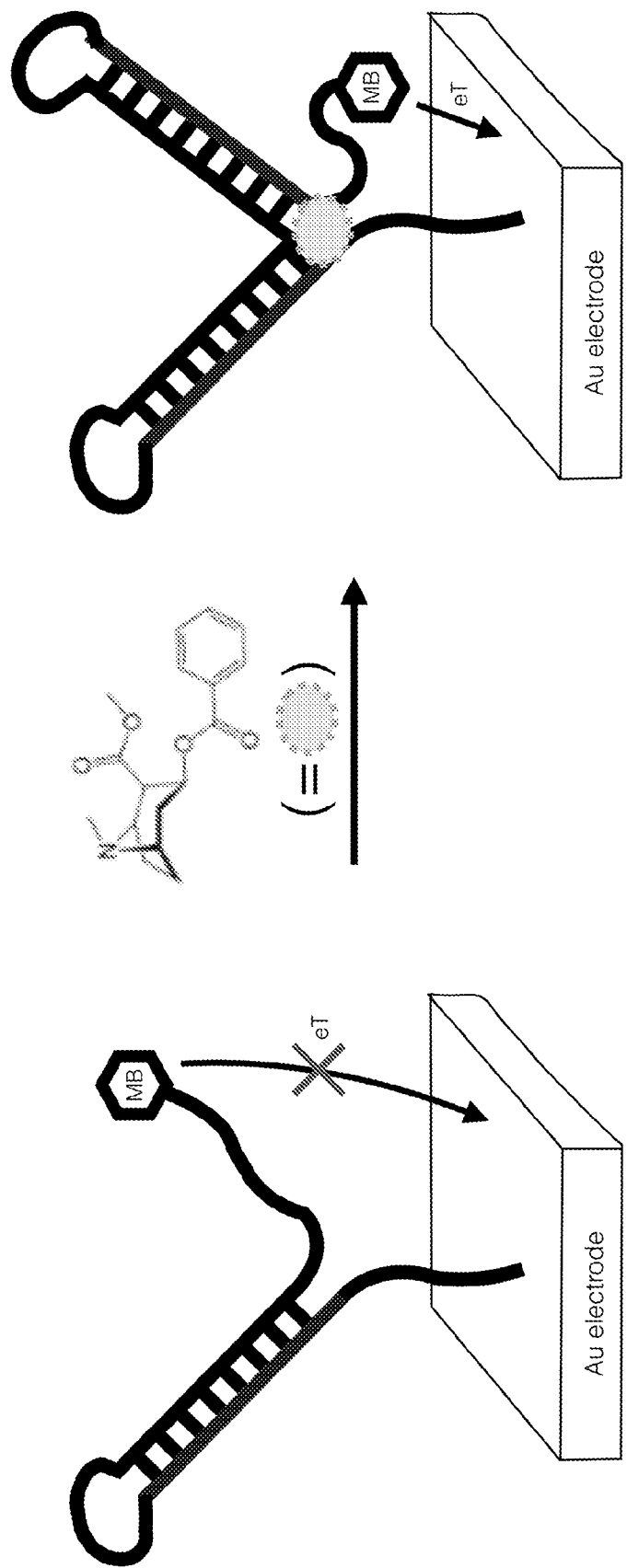
FIG. 16 is a schematic illustration of detection of detection of cocaine or procaine with an electrochemical aptamer biosensor according to one or more embodiments.

Further E-DNA can be used to detect small molecules 334. In this case, as shown in FIG. 16, the probe molecule on the working electrode 330 surface is an aptamer, a DNA or RNA molecule that has been selected in vitro to bind a specific molecular analyte, that changes its structure (folds) upon binding to its target analyte. Again the modified working electrode 330 is attached to a potentiostat 335 with a platinum counter 310 and a silver/silver chloride reference electrode 320. Square wave voltammetry is performed as described in FIG. 10014. A peak should be seen around −0.35 V, which is saved as the background measurement and registered by the MCU 340 (done during fabrication). Once VF reaches the E-DNA the height of the peak at −0.35 V will change. The magnitude of this change is related to the concentration of the target analyte.

To ensure equal flow rate through the channel 170, and ensure an equal amount of VF delivered to a biosensor 200 (electrochemical/colorimetric/E-DNA etc.) bifurcation of fluid channeling is ideal which is illustrated in FIG. 10018. Each of the channels could be coated with specific molecules to treat or filter or detect certain molecules in the VF as described in FIG. 18. At the end of the channel 170 there will either be a 200 biosensor with electrodes, or just a vaginal fluid holder 270 which functions as a placeholder for fluids drawn over the various reaction zones 265, 266 and 267.

Once there is a secure connection established between the SMP and the device, the platform will through a mobile device application visualize the results from the biosensor analysis. As the data is being transmitted to the device, it is once received by the app decrypted using the special passcode key 490, associated with the SMPs UID. Not all data from the bio-sensor analysis is presented to the user; this depends on the sensitivity of the data. Data describing e.g. diseases (such as STDs, HIV, cancers etc.), may not be presented to the user, but is instead either sent to a medical professional 610, or presented by a notification on the users screen 530, letting her know she should seek assistance from a medical professional for further analysis.

As data is transmitted to the device, various information is being stored in the app. The specific location 521 of the device is collected (via e.g. GPS, IP or Wi-Fi), a timestamp 522 of the analysis and meta data 523 descripting what version of the software that both the device and the SMP is using. In the application the users former history 524 is also being accessed, just as the new bio-sensor information is stored in the user history. In the app the user also has a profile 525, describing e.g. the age, ethnicity, height, weight and other information, describing the user. Connected to 525 is also a set of questionnaires, which can prompt the user to ask about e.g. her sexual activities, her exercise patterns, eating patterns or other questions related to her behavior or health. As all data on the device is sensitive, it is when on the device also encrypted using encryption software 526.

The data presented to the user can be e.g. a visual interpretation of data on the device display 530. This can be e.g. graphs indicating how values of e.g. iron has been changing over time, but could also be on/off indicators next to biomarkers or groups of biomarkers, indicating if something might be off, also notifying the user to seek medical assistance.

The data from the device can also be send from the device to either a cloud service 600, or directly to a medical professional 610. If the information is send to a medical professional, the information can be send to either a dedicated platform at which the medical professional can login with special login details, or directly to a third-party service 611 used by the medical professional. The medical professional can depending on access levels have access to e.g. all sensor data 524, the users profile information 525 and other data from the SMP platform and user app. Based on this information the medical professional can also provide feedback 612 back to the user, letting the user know of a e.g. a new medical appointment, drug-prescriptions or similar.

The data from the app will also be encrypted and send to a cloud service 600. The data will be stored in a cloud-database 620, from which the user can also always download the data back to the device. From the database it is further possible to do data aggregation 621 across all users of the platform, looking for specific patterns in health. As the data is stored in a database, third party vendors 640 may also be permitted for various access to data streams, most fully anonymized.

Figure 5:
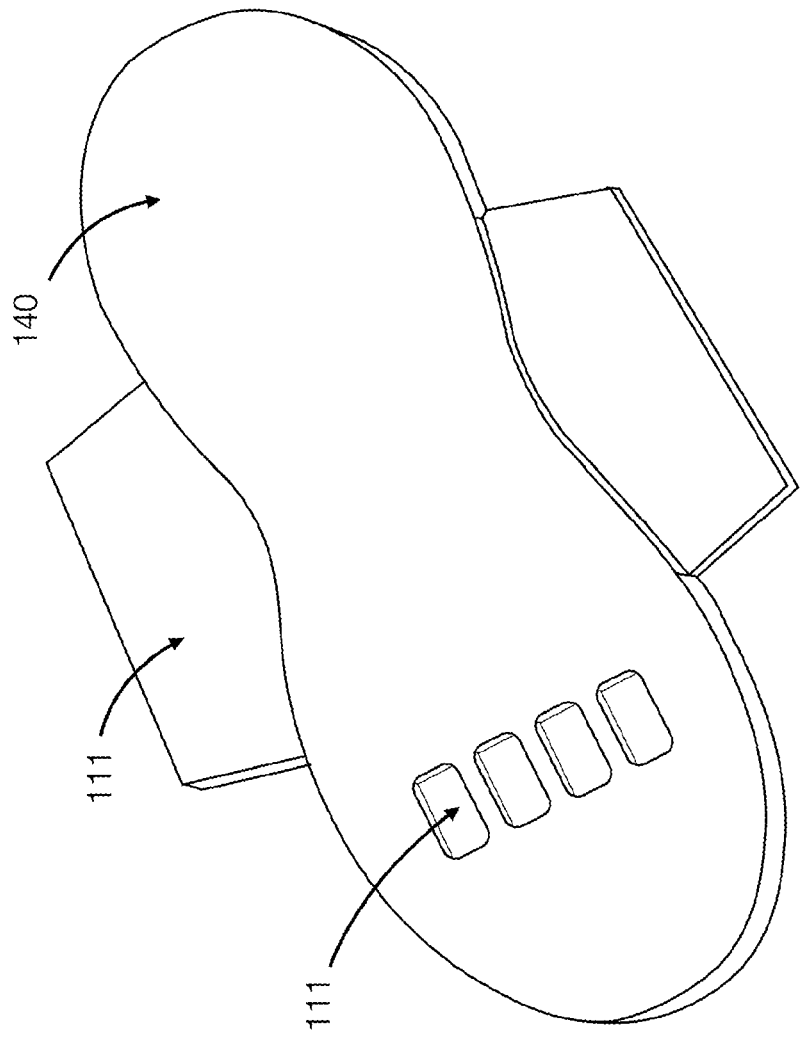
FIG. 5 is a schematic illustration of another aspect of the invention using colorimetric and visual detection on the backside of the pad according to one or more embodiments.
Figure 17:
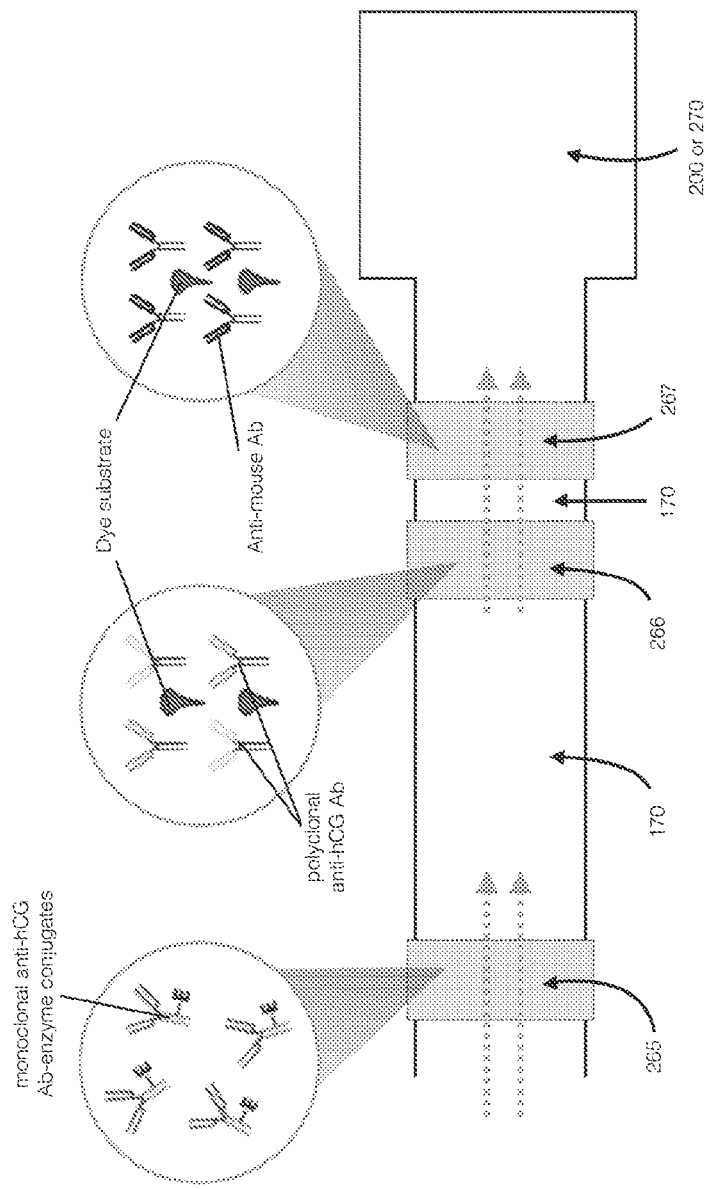
FIG. 17 is a schematic illustration of detection of colorimetric detection—backside of menstrual pad according to one or more embodiments.
Figure 18:
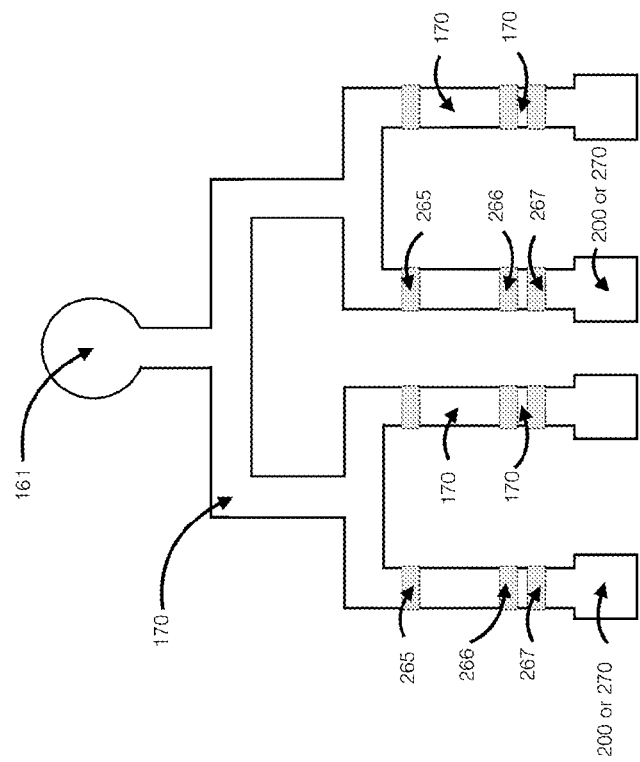
FIG. 18 is a schematic illustration of a binary bifurcator for distribution of a fluidic flow in an electrochemical detection system according to one or more embodiments.
Figure 19:
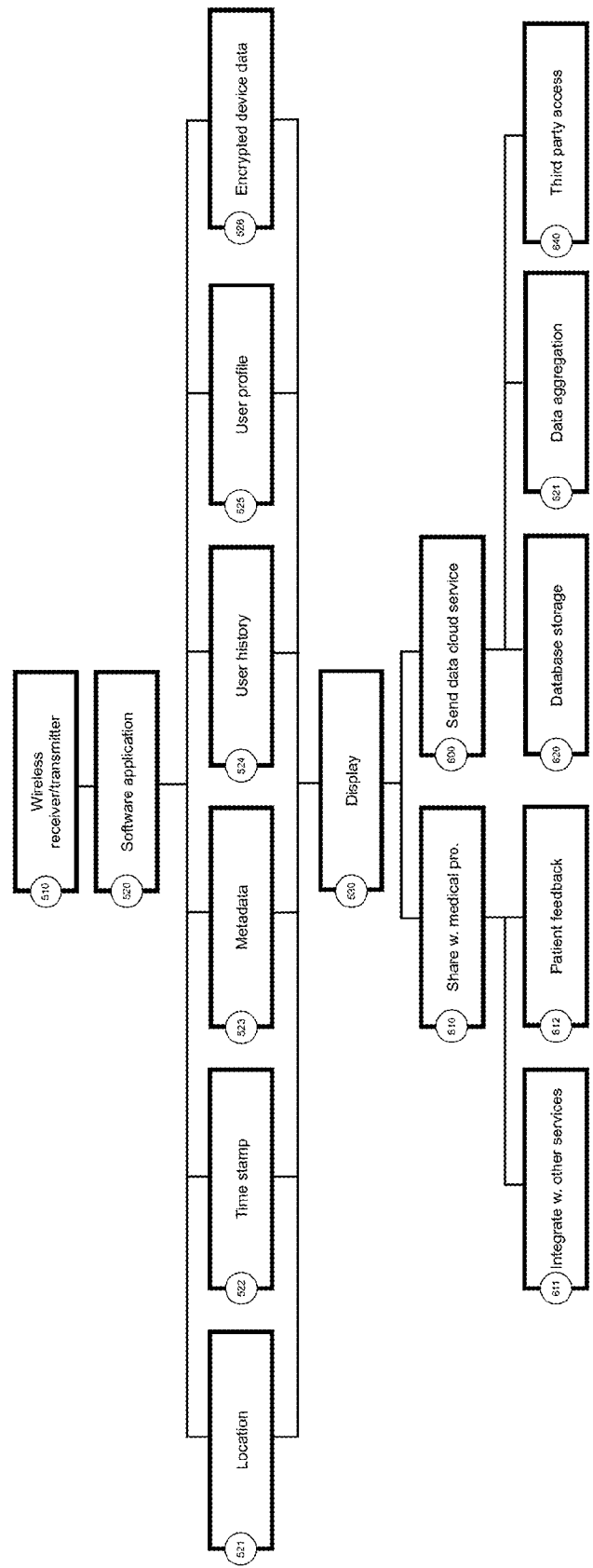
FIG. 19 is a schematic illustration showing the transmission and processing of data from the electrochemical detection system to an external device according to one or more embodiments.

Another version of the bottom layer of a pad is shown in FIG. 5. This solution excludes the need for microelectronics by using colorimetric detection which in case of biomarker detection will lead to a color change show in windows on the backside of the pad. For detecting quantities of certain biomarker levels, where only the presence is not enough information, a smartphone with camera will be needed or a colorimetric reference will be shown in the package similar to what is used for reading amounts of H+ when doing pH-measurements. Results will be shown in the mobile device application on a device 400 or 500. The biosensor platform for colorimetric detection is illustrated in FIG. 17. In the channeling system 170 a specific location may be coated with a specific molecule (e.g. an antibody for a target antigen in the VF). Once the VF flows through the channels (if paper fluidics this will be due to capillary force) 170 and reaches and soaks the first reaction zone 265, antigens in the VF binds to the antibodies which have been put on this location. Because these are not immobilized, antibody-antigen molecules as well as antibodies which has not reacted with an antigen will flow by capillary force to reaction zone 2 where anti-antibodies are. These are not able to move and will bind to all the antibodies which has not reacted with an antigen. Only the antibody-antigen molecules will continue its flow to a third reaction zone where either an colorimetric or electrochemical detection can take place. In the case of colorimetric detection the color change will be shown on the back side of the pad as it is illustrated in FIG. 5.

These female hygiene products can produced at one new product but also can the microfluidic electrochemical device platform be incorporated into existing products on the market.

Among other advantages our feminine smart pad reduces the required sample volume and amount of reagents compared to conventional laboratories, it shortens the time of reactions and decreases amount of biohazard waste for disposal.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments. Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise.

It will be appreciated that while a particular sequence of steps has been shown and described for purposes of explanation, the sequence may be varied in certain respects, or the steps may be combined, while still obtaining the desired configuration. Additionally, modifications to the disclosed embodiment and the invention as claimed are possible and within the scope of this disclosed invention.

The invention claimed is:

1. A vaginal fluid monitoring device, comprising:
an absorbent layer, wherein the absorbent layer is configured to be in proximity to flow of vaginal fluid;
an electrochemical detection system configured to obtain data regarding at least one analyte in a vaginal fluid, said electrochemical detection system in fluid communication with the absorbent layer;
a fluid-impermeable layer disposed between the absorbent layer and the electrochemical detection system; and
a fluid channeling system disposed between the fluid-impermeable layer and the electrochemical detection system to deliver the vaginal fluid to the electrochemical detection system through said fluid-impermeable layer;
wherein the fluid-impermeable layer comprises at least one inlet in fluid communication with the absorbent layer and the fluid channeling system; and
wherein the vaginal fluid monitoring device is configured to be coupled with one of the following: a feminine hygiene product, a diaper or an adult incontinence product.

2. The vaginal fluid monitoring device of claim 1 wherein said electrochemical detection system comprises a biosensor to detect said analyte in the vaginal fluid and an electrode in electrical communication with said biosensor, said electrode detecting changes in at least one of current, impedance or voltages in the detected analyte and generating an electrical signal indicative of said changes in said detected analyte.

3. The device of claim 2, further comprising a microfluidic system for directing the vaginal fluid to the biosensor; and microelectronic circuitry for detecting and processing said signal generated by said biosensor electrode.

4. The device of claim 3 further comprising a transceiver for wirelessly transmitting said processed signal from said biosensor electrode.

5. The device of claim 1, further comprising a collection layer disposed between the absorbent layer and the electrochemical detection system, the collection layer comprising one or more fluidic pathways for directing the vaginal fluid to the electrochemical detection system.

6. The device of claim 3, wherein one or more of the microfluidic system, biosensor and microelectronic circuitry are supported on a paper or plastic substrate.

7. The device of claim 3 wherein the microfluidic system comprises a plurality of microfluidic channels.

8. The device of claim 7, wherein the plurality of microfluidic channels are configured to direct the vaginal fluid to a single biosensor.

9. The device of claim 7, wherein the biosensor comprises a plurality of biosensors and each microfluidic channel is configured to direct the vaginal fluid to a different biosensor.

10. The device of claim 1, wherein the electrochemical detection system is configured to receive and analyze a plurality of samples.

11. The device of claim 1, wherein the electrochemical detection system is configured to sequentially process a plurality of samples.

12. The device of claim 2 wherein the biosensor comprises ligands capable of binding or chemically interacting with an analyte of interest.

13. The device of claim 2, wherein the analyte is a nucleic acid, an antibody or a small molecule, antigen, bacteria, viruses, parasites, fungus, minerals, vitamins, lipids.

14. The device of claim 1, wherein the device comprises computer readable instructions to encrypt data stored or transmitted from the electrochemical detection system.

15. The device of claim 3, wherein the microelectronic circuitry is configured in an open circuit, wherein the circuit closes on contact with a vaginal fluid.

16. The device of claim 1, wherein the feminine hygiene product is a pad or panty liner.

17. The device of claim 16, wherein the pad or panty liner further comprises a positioning element configured to maintain the absorbent layer in proximity to flow of vaginal fluid.

18. The device of claim 3, wherein the microprocessor of the microelectronic circuitry has read/write capability.

19. The device of claim 18, wherein the microprocessor is capable of software updates to encryption, date stamping, biosensor calibration, new test protocols.

20. A method for analyte detection in a vaginal fluid comprising: providing a vaginal fluid monitoring device according to claim 1; and collecting a vaginal fluid in the absorbent layer; directing the vaginal fluid into the electrochemical detection system; electrochemically analyzing the vaginal fluid in the electrochemical detection system; and wirelessly transmitting the information to a remote device.

21. The method of claim 20, wherein the biosensor comprises ligands that bind or chemically interact with an analyte of interest to cause a change of impedance or current or voltage.

22. The method of claim 20, wherein the information is transferred by radio frequency (rf), Bluetooth, Bluetooth LE, NFC, GSM, CDMA, http, https, e-SIM or Wi-Fi.

23. The method of claim 20, wherein there is a secure pairing between the vaginal fluidic monitoring device and the remote device.

24. The method of claim 20, wherein the remote device is the cloud, a personal computer or smartphone.

25. The vaginal fluid monitoring device of claim 1, further comprising a battery in an inactive state; packaging enclosing the device; and a switched operationally linked to the battery, for activating the battery on opening the package or removal of the device from the package.

26. The device of claim 4, wherein the microprocessor comprises machine readable instructions to disable the fluid monitoring device on completion of a transmission of test results to a remote device.

\* \* \* \* \*